United States Patent [19]

Morimoto et al.

[11] Patent Number: 5,304,565
[45] Date of Patent: Apr. 19, 1994

[54] NITROGEN CONTAINING HETEROCYCLIC COMPOUNDS, THEIR PRODUCTION AND USE

[75] Inventors: Akira Morimoto, Osaka; Kohei Nishikawa, Kyoto, both of Japan

[73] Assignee: Takeda Chemical Industries, Ltd., Osaka, Japan

[21] Appl. No.: 666,037

[22] Filed: Mar. 7, 1991

[30] Foreign Application Priority Data

| Mar. 7, 1990 | [JP] | Japan | 2-56205 |
| Mar. 7, 1990 | [JP] | Japan | 2-56206 |
| Mar. 20, 1990 | [JP] | Japan | 2-71051 |

[51] Int. Cl.$^5$ .................. A61K 31/44; A61K 31/505; C07D 213/63; C07D 239/90
[52] U.S. Cl. .................. 514/340; 514/259; 514/260; 514/269; 514/312; 514/345; 514/350; 514/351; 544/284; 544/287; 544/326; 544/328; 544/329; 546/153; 546/276; 546/298; 546/300; 546/301; 546/302
[58] Field of Search .............. 544/283, 287, 153, 276; 514/259, 261, 312, 340, 345, 350, 351; 546/153, 276, 298, 300, 301, 302

[56] References Cited

U.S. PATENT DOCUMENTS

| 4,668,682 | 5/1987 | Sekiya et al. | 514/259 |
| 4,880,804 | 11/1989 | Carini et al. | 514/234.5 |
| 5,100,897 | 3/1992 | Allen et al. | 514/269 |
| 5,166,206 | 11/1992 | Allen et al. | 514/269 |
| 5,240,928 | 8/1993 | Allen et al. | 514/259 |

FOREIGN PATENT DOCUMENTS

| 0028833 | 5/1981 | European Pat. Off. |
| 0028834 | 5/1981 | European Pat. Off. |
| 0245637 | 11/1987 | European Pat. Off. |
| 0253310 | 1/1988 | European Pat. Off. |
| 0291969 | 11/1988 | European Pat. Off. |
| 0323841 | 7/1989 | European Pat. Off. |
| 407342 | 1/1991 | European Pat. Off. |
| 411766 | 2/1991 | European Pat. Off. |

OTHER PUBLICATIONS

Chiu et al., European Journal of Pharmacology 157:13-21 (1988).

Primary Examiner—Mukund J. Shah
Assistant Examiner—Matthew V. Grumbling
Attorney, Agent, or Firm—Wegner, Cantor, Mueller & Player

[57] ABSTRACT

Nitrogen-containing heterocyclic compounds of the formula (I):

wherein Y is N or CH; $R^1$, which may be optionally bound through a hetero atom, is a hydrocarbon residue which may be substituted; $R^2$ and $R^3$ which may be same or different, are each independently hydrogen, cyano, nitro, optionally substituted lower alkyl, or —COD wherein D is alkoxy, hydroxy, halogen, or optionally substituted amino: or $R^2$ and $R^3$ are taken together to form a benzene ring which may be substituted; the dotted line is a chemical bond; Z is bound to a hetero nitrogen atom and is a group having the formula:

wherein $R^4$ is hydrogen, halogen or nitro, and $R^5$ is a residue capable of forming an anion or a residue convertible into an anion; A is a direct bond or a spacer having atomic length of two or less between the phenylene group and the phenyl group; and n is an integer of 1 or 2; and the pharmaceutically acceptable salts thereof, have potent angiotensin II antagonist activity and antihypertensive activity, thus being useful as therapeutic agents for treating circulatory system diseases such as hypertensive diseases, heart diseases, strokes, etc.

23 Claims, No Drawings

NITROGEN CONTAINING HETEROCYCLIC COMPOUNDS, THEIR PRODUCTION AND USE

FIELD OF THE INVENTION

The present invention relates to novel nitrogen-containing heterocyclic compounds having potent pharmacological activity and intermediates for the preparation thereof. More particularly, the present invention relates to compounds having potent anti-hypertensive activity and angiotensin II antagonist activity, which are useful as therapeutic agents for treating circulatory diseases such as hypertensive diseases, heart diseases, strokes, etc.

BACKGROUND OF THE INVENTION

The renin-angiotensin system is involved in the homeostatic function to control systemic blood pressure, the volume of body fluid, balance among the electrolytes, etc., associated with the aldosterone system. Development of angiotensin II converting enzyme inhibitors (ACE inhibitor) (this converting enzyme produces angiotensin II which possesses strong vasoconstrictive activity) has clarified the relation between the renin-angiotensin system and hypertension. Since angiotensin II elevates blood pressure via the angiotensin II receptors on cell membranes, angiotensin II antagonists as well as the ACE inhibitor would be useful in treating hypertension.

It has been reported that various angiotensin II analogues such as saralasin, [$Sar^1$,$Ile^8$]A II, and the like, possess potent angiotensin II antagonist activity.

It has, however, been reported that, when peptide antagonists are administered parenterally, their actions are not prolonged and, when administered orally, they are ineffective (M. A. Ondetti and D. W. Cushman, Annual Reports in Medicinal Chemistry, 13, 82–91 (1978)).

Non-peptide angiotensin II antagonists are disclosed in Japanese Patent Laid Open No. 71073/1981; No. 71074/1981; No. 92270/1982; No. 157768/1983; No. 240683/1987; No. 23868/1988; and No. 117876/1989, and European Patent Laid Open No. 0323841, etc.

Imidazole derivatives having angiotensin II antagonist activity are disclosed in A. T. Chiu et al., Eur. J. Pharm., 157, 13 (1981), P. C. Wong et al., J. Pharmcol. Exp. Ther., 247, 1 (1988), P. C. Wong et al., Hypertension, 13, 489 (1989), etc.

Allen, U.S. Pat. No. 5,100,897, discloses pyrimidinones stated to be angiotensin II antagonists.

SUMMARY OF THE INVENTION

The present inventors made extensive investigations to prepare useful compounds which have angiotensin II antagonist activity. As a result of this research, the present inventors have succeeded in synthesizing nitrogen-containing heterocyclic compounds possessing highly potent angiotensin II antagonist activity and developed the present invention.

The present invention provides nitrogen-containing heterocyclic compounds having the formula I:

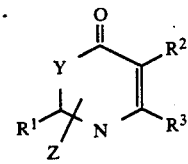

wherein
Y is CH;
$R^1$, which may be optionally bound through a hetero atom, is a hydrocarbon residue which may be substituted;
$R^2$ and $R^3$ which may be same or different, are each independently hydrogen, cyano, nitro, optionally substituted lower alkyl, or —COD wherein D is alkoxy, hydroxy, halogen, or optionally substituted amino; or $R^2$ and $R^3$ are taken together to form a benzene ring which may be substituted;
the dotted line is a chemical bond;
Z is bound to a hetero nitrogen atom and is a group having the formula:

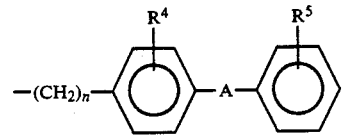

wherein
$R^4$ is hydrogen, halogen or nitro, and
$R^5$ is a residue capable of forming an anion or a residue convertible into an anion;
A is a direct bond or a spacer having atomic length of two or less between the phenylene group and the phenyl group; and
n is an integer of 1 or 2;
and the pharmaceutically acceptable salts thereof.

These compounds are potent angiotensin II antagonists which are of value in the treatment of circulatory system diseases such as hypertensive diseases, heart diseases, strokes, etc.

Another aspect of the present invention relates to pharmaceutical compositions comprising an effective amount of the nitrogen-containing heterocyclic compound having the formula I and a pharmaceutically acceptable carrier useful in treating circulatory system diseases such as hypertensive diseases, heart diseases, strokes, etc., and processes for preparing such compounds and compositions.

Still another aspect of the present invention relates to a method for treating said circulatory system diseases of patients, which comprises administering an effective amount of the nitrogen-containing heterocyclic compound having the formula I or the pharmaceutical composition thereof to the patient.

DETAILED DESCRIPTION OF THE INVENTION

The present invention provides nitrogen-containing heterocyclic compounds having the formula I and the pharmaceutically acceptable salts thereof, which possess potent angiotensin II antagonist activity and are of value in the treatment of circulatory diseases such as hypertensive diseases, heart diseases, strokes, etc., pharmaceutical compositions comprising an effective amount of the nitrogen-containing heterocyclic compound having the formula I and a pharmaceutically acceptable carrier useful in treating said circulatory diseases and processes for preparing such compounds and compositions.

The present invention further provides a method for treating said circulatory system diseases of patients, which comprises administering an effective amount of the nitrogen-containing heterocyclic compound having the formula I or the pharmaceutical composition thereof to the patient.

An important group of compounds according to the present invention are the compounds of the formula Ia:

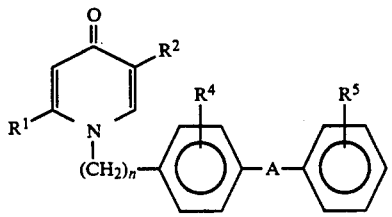

wherein
 $R^1$, which may be optionally bound through a hetero atom, is a hydrocarbon residue which may be substituted;
 $R^2$ is —COD wherein D is alkoxy, hydroxy, halogen, or optionally substituted amino;
 $R^4$ is hydrogen, halogen or nitro;
 $R^5$ is a residue capable of forming an anion or a residue convertible into an anion;
 A is a direct bond or a spacer having atomic length of two or less between the phenylene group and the phenyl group; and
 n is an integer of 1 or 2;
and the pharmaceutically acceptable salts thereof.

With regard to the foregoing formula (I), hydrocarbon residues for $R^1$, which may be optionally bound through a hetero atom such as a nitrogen, oxygen, or sulfur atom, include acyclic hydrocarbon residues such as lower alkyls of 1 to 8 carbon atoms (e.g. methyl, ethyl, propyl, isopropyl, butyl, isobutyl, sec-butyl, t-butyl, pentyl, i-pentyl, hexyl, heptyl, octyl, and the like), lower alkenyls of 2 to 8 carbon atoms (e.g. vinyl, allyl, isopropenyl, 2-butenyl, 1,3-butadienyl, 2-pentenyl, 2-hexenyl, 2-octenyl, and the like), and lower alkynyls of 2 to 8 carbon atoms (e.g. ethynyl, 2-propynyl, 2-butynyl, 2-pentynyl, 2-octynyl, and the like); cyclic hydrocarbon residues such as alicyclic hydrocarbon residues of 3 to 8 carbon atoms (e.g. cyclopropyl, cyclopentyl, cyclohexyl, 2-cyclohexen-1-yl, cyclooctyl and the like), aromatic hydrocarbon residues of about 6 to 12 carbon atoms (e.g. phenyl, naphthyl and the like); etc.

Said hydrocarbon residues for $R^1$ may be optionally substituted with hydroxyl, lower ($C_{1-4}$) alkoxy (e.g. methoxy, ethoxy, and the like), lower ($C_{1-4}$) alkyl (e.g. methyl, ethyl, and the like), halogen (e.g. F, Cl, Br and the like), nitro, optionally substituted amino such as amino, N-lower ($C_{1-4}$) alkyl amino (e.g. methylamino, ethylamino, etc.), N,N-dilower ($C_{1-4}$) alkyl amino (e.g. dimethylamino, diethylamino, etc.), N-arylamino (e.g. phenylamino, naphthylamino, etc.), N-aralkylamino (e.g. benzylamino, naphthylmethyl-amino, etc.) and alicyclic amino (e.g. morpholino, piperidino, piperazino, piperidylmethyl, N-phenylpiperazino, N-(p-fluorophenyl)piperazino, N-(m-methoxyphenyl)-piperazino, etc.), acyloxy such as lower ($C_{1-4}$) alkanoyloxy (e.g. acetyloxy, etc.) and aroyloxy (e.g. benzoyloxy, etc.), aryl such as phenyl and naphthyl (e.g. phenyl which may be optionally substituted with halogen, nitro, lower ($C_{1-4}$) alkoxy, lower ($C_{1-4}$) alkyl or the like at an optional position on the benzene ring), or the like. Substituents on the hydrocarbon residue for $R^1$ may be taken together to form heteroaryl such as 5-methyl-2-thienyl.

Where $R^2$ and $R^3$ are each independently a group having the formula: —COD, alkoxy groups for D include lower ($C_{1-4}$) alkoxy (e.g. methoxy, ethoxy, and the like). For D, examples of halogen include Cl, Br and the like, and examples of optionally substituted amino include amino, N-lower ($C_{1-4}$) alkyl amino (e.g. methylamino, ethylamino, propylamino, and the like), N,N-dilower ($C_{1-4}$) alkyl amino (e.g. dimethylamino, diethylamino, and the like), N-arylamino (e.g. anilino, N-methylanilino, and the like), N-aralkylamino (e.g. benzylamino, phenethyl, naphthylmethylamino, and the like), N-heteroarylamino (e.g. pyridylamino, and the like), N-heteroaralkylamino (e.g. pyridylmethylamino, and the like), alicyclic amino (e.g. morpholino, piperidino, piperazino, piperidylmethyl, N-phenylpiperazino, N-(p-fluorophenyl)piperazino, and the like), wherein said alkyl, aryl and heteroaryl groups may be optionally substituted with lower ($C_{1-4}$) alkyl (e.g. methyl, ethyl, propyl, isopropyl, butyl, isobutyl, sec-butyl, and the like), hydroxyl, optionally substituted amino (e.g. amino, N-lower ($C_{1-4}$) alkyl amino (e.g. methylamino, ethylamino, and the like), N,N-dilower ($C_{1-4}$) alkyl amino (e.g. dimethylamino, and the like), alicyclic amino (e.g. morpholino, piperidino, piperazino, N-phenylpiperazino, and the like)), halogen, nitro, lower ($C_{1-4}$) alkoxy (e.g. methoxyl, ethoxyl), or the like.

The compounds wherein D is halogen are useful as synthetic intermediates for the preparation of those wherein D is alkoxy or optionally substituted amino.

Lower alkyl groups for $R^2$ and $R^3$ are preferably lower alkyls of 1 to 8 carbon atoms which may be straight or branched.

Examples of such alkyl groups for $R^2$ and $R^3$ include methyl, ethyl, propyl, isopropyl, butyl, isobutyl, sec-butyl, t-butyl, pentyl, i-pentyl, hexyl, heptyl, 2-octyl, and the like.

Said alkyl groups for $R^2$ and $R^3$ may be optionally substituted with hydroxyl, lower ($C_{1-4}$) alkoxy (e.g. methoxyl, ethoxyl, and the like), optionally esterified carboxyl (e.g. lower ($C_{1-4}$) alkoxycarbonyl such as methoxycarbonyl), lower ($C_{1-4}$) alkyl (e.g. methyl, ethyl, etc.), halogen (e.g. F, Cl, Br and the like), nitro, optionally substituted amino such as amino, N-lower ($C_{1-4}$) alkyl amino (e.g. methylamino, ethylamino, etc.), N,N-dilower ($C_{1-4}$) alkyl amino (e.g. dimethylamino, diethylamino, etc.), acyloxy such as lower ($C_{1-4}$) alkanoyloxy (e.g. acetyloxy, etc.) and aroyloxy (e.g. benzoyloxy, etc.), aryl such as phenyl and naphthyl (e.g. phenyl which may be optionally substituted with halogen, nitro, lower ($C_{1-4}$) alkoxy, lower ($C_{1-4}$) alkyl or the like at an optional position on the benzene ring), or the like.

When $R^2$ and $R^3$ are taken together to form a benzene ring, the benzene ring may be optionally substituted, for example, with
 halogen (e.g. F, Cl, Br and the like);
 nitro;
 cyano;
 optionally substituted amino such as amino, N-lower ($C_{1-4}$) alkyl amino (e.g. methylamino, ethylamino, etc.), N,N-dilower ($C_{1-4}$) alkyl amino (e.g. dimethylamino, diethylamino, etc.), N-arylamino (e.g. phenylamino, naphthylamino, etc.), N-aralkylamino (e.g. benzylamino, naphthylmethyl-amino, etc.) and alicyclic amino (e.g. morpholino, piperidino, piperazino, piperidylmethyl, N-phenylpiperazino, N-(p-fluorophenyl)piperazino, N-(m-methoxyphenyl)piperazino, etc.);

a group having the formula: —W—$R^6$ [wherein W is a chemical bond, —O—, or —S— and $R^6$ is hydrogen, optionally substituted lower ($C_{1-4}$) alkyl as defined above (e.g. hydroxyalkyl, lower ($C_{1-4}$) alkoxyalkyl, halogenoalkyl, acyloxyalkyl, acylalkyl, lower alkoxycarbonylalkyl, N-substituted carbamoylalkyl, optionally substituted aminoalkyl such as aminoalkyl, N-lower ($C_{1-4}$) alkyl aminoalkyl (e.g. methylaminoalkyl, ethylaminoalkyl, etc.), N,N-dilower ($C_{1-4}$) alkyl aminoalkyl (e.g. dimethylaminoalkyl, diethylaminoalkyl, etc.), N-arylaminoalkyl (e.g. phenylaminoalkyl, etc.) and alicyclic aminoalkyl (e.g. morpholinoalkyl, piperidinoalkyl, piperazinoalkyl, N-phenylpiperazinoalkyl, etc.), or acyl as defined above (e.g. lower ($C_{1-4}$) alkanoyl, optionally substituted arylcarbonyl, optionally substituted heteroarylcarbonyl, etc.)];

or a group having the formula: —CO—D' wherein D' is optionally substituted lower ($C_{1-4}$) alkyl as defined above, optionally substituted aryl as previously defined (e.g. phenyl, naphthyl, etc.), optionally substituted lower ($C_{1-4}$) alkoxy (e.g. lower ($C_{1-4}$) alkoxy which may be optionally substituted with hydroxyl, optionally substituted amino as defined above, halogen (e.g. F, Cl, Br and the like), lower ($C_{1-4}$) alkoxy, or the like on the alkyl moiety), optionally substituted amino such as amino, N-lower ($C_{1-4}$) alkyl amino (e.g. methylamino, ethylamino, etc.), N,N-dilower ($C_{1-4}$) alkyl amino (e.g dimethylamino, diethylamino, etc.), N-arylamino (e.g. phenylamino, naphthylamino, etc.), and alicyclic amino (e.g. morpholino, piperidino, piperazino, N-phenylpiperazino, etc.), halogen (e.g. F, Cl and the like) or hydroxyl.

When the benzene ring is substituted with the group having the formula: —CO—D', the compounds wherein D' is halogen are useful as synthetic intermediates for the preparation of those wherein D is optionally substituted alkoxy or amino.

With regard to the compounds (Ic), the optionally substituted benzene ring for the ring B is as defined above for $R^2$ and $R^3$ taken together.

$R^4$ represents hydrogen, halogen (e.g. chlorine, bromine, and the like) or nitro, and may be in the ortho or meta position to the —A— group. Among them, hydrogen is most preferable.

Examples of residues capable of forming an anion and residues convertible into the anion for $R^5$ include carboxyl, lower ($C_{1-4}$) alkoxycarbonyl, cyano, tetrazolyl, trifluoromethanesulfonic amide (—$NHSO_2CF_3$), phosphoric acid, sulfonic acid, and the like. Such residues may include those which are capable of forming anions or convertible into anions either chemically or under biological and/or physiological conditions. $R^5$ is in any positions on the phenyl group. Among them, carboxyl and tetrazolyl are preferred. $R^5$ is preferably in the ortho position. The compounds wherein $R^5$ is a residue capable of forming an anion or convertible thereinto chemically (e.g. by oxidation, reduction or hydrolysis) (e.g. cyano and the like), are useful as synthetic intermediates.

A shows that the adjacent phenylene group is bonded to the phenyl group directly or through a spacer whose atomic chain is 2 or less. As the spacer, any one can be exemplified, so long as it is a divalent chain in which the number of atoms constituting the straight chain is 1 or 2, and it may have a side chain. Examples of such spacers include lower ($C_{1-4}$) alkylene,

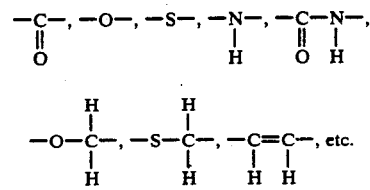

When Y is CH, the dotted line represents a chemical bond between Y and the carbon atom to which $R^1$ is attached.

A preferred embodiment of the invention is a compound of the formula (Ia'):

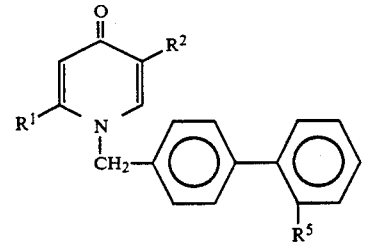

wherein $R^1$ is lower ($C_{1-8}$) alkyl; $R^2$ is —COD wherein D is halogen; lower ($C_{1-4}$) alkoxy, hydroxy, or optionally substituted amino (inter alia lower ($C_{1-4}$) alkyl); and $R^5$ is carboxyl or tetrazolyl (inter alia tetrazolyl); and the pharmaceutically acceptable salts thereof.

Among the compounds of the above formula (I), those of the formula (I')

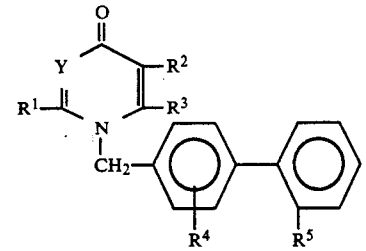

wherein $R^1$, which may be optionally bound through a hetero atom, is optionally substituted lower ($C_{1-4}$) alkyl; $R^2$ and $R^3$ are taken together to form an optionally substituted benzene ring; Y is N or CH; $R^4$ is hydrogen; and $R^5$ is tetrazolyl; and the pharmaceutically acceptable salts thereof are preferable.

The compounds (I) of the present invention may be prepared by several reaction schemes, as illustrated below for a preferred compound.

Scheme A

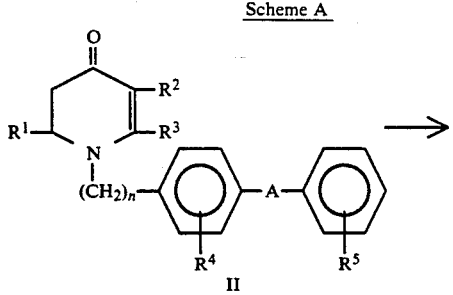

wherein $R^1$, $R^2$, $R^3$, $R^4$, $R^5$, A and n have the above-defined meanings.

Scheme G

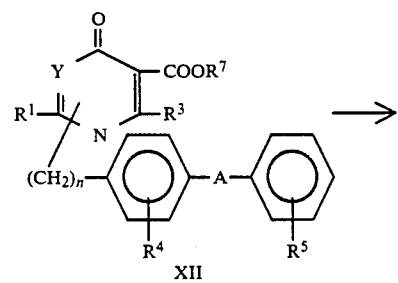

wherein $R^1$, $R^2$, $R^3$, $R^4$, A, Y, n and the dotted line are as defined above.

Scheme H

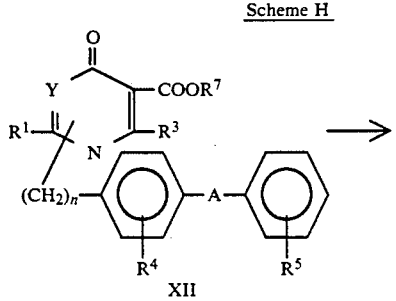

Scheme H

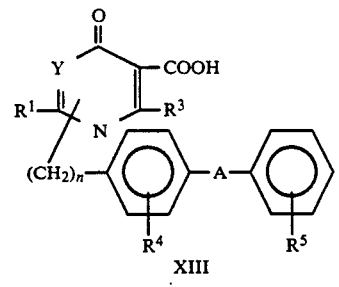

wherein $R^1$, $R^3$, $R^4$, $R^5$, A, Y, n and the dotted line are as defined above and $R^7$ is lower ($C_{1-4}$) alkyl.

Scheme I wherein $R^1$, $R^3$, $R^4$, $R^5$, $R^7$, A, Y, n and the dotted line are as defined above and $R^8$ and $R^9$ are each independently hydrogen or a hydrocarbon residue (e.g. lower ($C_{1-4}$) alkyl and optionally substituted aryl).

Scheme J

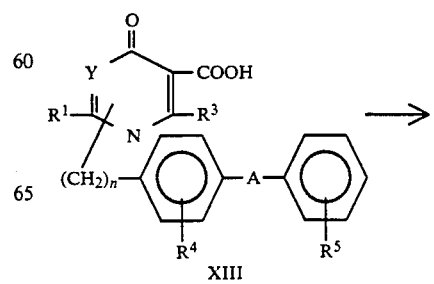

-continued
Scheme J

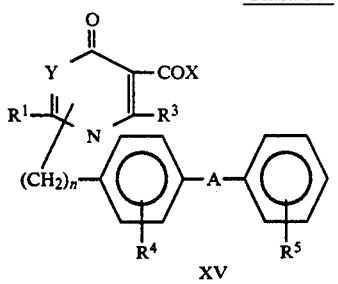

wherein $R^1$, $R^3$, $R^4$, $R^5$, A, Y, n and the dotted line are as defined above and X is halogen.

Scheme K

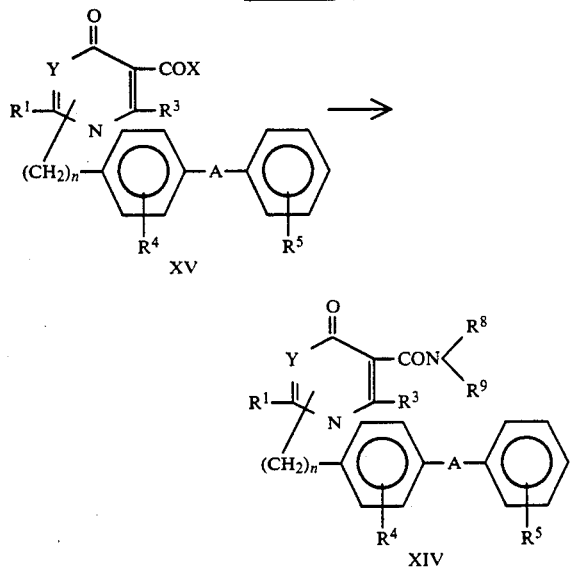

wherein $R^1$, $R^3$, $R^4$, $R^5$, $R^8$, $R^9$, X, A, Y, n and the dotted line are as defined above.

In Scheme A, the compound (II) is reacted with an oxidizing agent to form the compound (Ia). One molar portion of the compound (II) is employed with approximately 1 to 3 moles of the oxidizing agent. The reaction is conventionally conducted in solvents such as benzene, toluene, tetrahydrofuran and dioxane. Examples of such oxidizing agents include 2,3-dichloro-5,6-dicyano-1,4-benzoquinone (DDQ), chloranil, and the like. Advantageously, the reaction is carried out at room temperature $-100°$ C. for 5 minutes–3 hours.

The cyano substituent on the benzene of the compounds (X) is reacted with various azides to form the tetrazole compounds (XI) as illustrated in Scheme G. One molar portion of the compound (X) is employed with 1-10 moles of the azide. The reaction is conventionally conducted in solvents such as dimethylformamide, dimethylacetamide, toluene, benzene, and the like. Examples of such azides include trialkyl-tin azide, triphenyl-tin azide, hydrogen azide, and the like. In the case where the organo-tin azide compound is employed, the reaction is carried out in toluene or benzene by heating under reflux for a period of from 10-30 hours. When the hydrogen azide is used, 5 moles of sodium azide and ammonium chloride per compound (X) are employed and the reaction is conducted in dimethylformamide at $100°$ C.–$130°$ C. for 1-10 days. During this reaction, it is preferable to facilitate working by adding an appropriate amount of sodium azide and ammonium chloride.

The reaction as illustrated in Scheme H is hydrolysis of the ester (XII) into the carboxylic acid (XIII) in the presence of an alkali. One molar portion of the compound (XII) is employed with 1 to 3 moles of the alkali. The reaction is conventionally conducted in solvents such as alcohols containing water (e.g. methanol, ethanol, methylcellosolve, and the like). Examples of such alkalis include sodium hydroxide, potassium hydroxide, and the like. The reaction is preferably conducted at room temperature $-100°$ C. for 1–10 hours.

The compounds (XII) are reacted with various amines to form the amide compounds (XIV) as illustrated in Scheme I. One molar portion of the compound (XII) is employed with about 2 to 50 moles of the amine. The reaction is conventionally conducted in solvents such as alcohols (e.g. methanol, ethanol, and the like) or without a solvent. The reaction is preferably conducted at a temperature in the range from room temperature to $200°$ C. Examples of such amines include ammonia, alkylamines (e.g. methylamine, ethylamine, propylamine, dimethylamine, diethylamine, butylamine, hydroxyethylamine, etc.), aralkylamines (e.g. benzylamine, phenetylamine, N-benzyl-N-methylamine, o-methoxy-benzylamine, etc.), arylamines (e.g. aniline, N-methylaniline, etc.), heteroaralkylamines (e.g. 2-, 3- or 4-pyridylmethylamine, etc.), alicyclic amines (e.g. morpholine, piperidine, piperazine, N-phenylpiperazine, 2-piperidylmethylamine, 3-(p-fluorophenylpiperazino)propylamine, etc.), and the like.

The compounds (XIII) are treated with various halogenating agents to form the acid halides (XV) as illustrated in Scheme J. One molar portion of the compound (XIII) is employed with about 1 to 5 moles of the halogenating agent. The reaction is conventionally conducted in solvents such as halogenated hydrocarbons (e.g. $CHCl_3$, $CH_2Cl_2$, $ClCH_2CH_2Cl$, and the like), ethers (e.g. tetrahydrofuran, dioxane, and the like) and aromatic hydrocarbons (e.g. benzene, toluene, and the like). Examples of such halogenating agents include oxalyl chloride, thionyl chloride, phosphorous oxychloride, phosphorous trichloride, phosphorous pentachloride, etc. The reaction is preferably conducted at room temperature $-100°$ C. for 1–10 hours.

The acid halides (XV) are reacted with various amines to form the amide compounds (XIV) as illustrated in Scheme K. One molar portion of the compound (XV) is employed with about 2 to 50 moles of the amine. The reaction is conventionally conducted in solvents such as alcohols (e.g. methanol, ethanol, and the like) and ethers (e.g. ethyl ether, tetrahydrofuran, dioxane, and the like). Examples of such amines include ammonia, alkylamines (e.g. methylamine, ethylamine, propylamine, dimethylamine, diethylamine, butylamine, hydroxyethylamine, etc.), aralkylamines (e.g. benzylamine, phenethylamine, N-benzyl-N-methylamine, o-methoxybenzylamine, etc.), arylamines (e.g. aniline, N-methylaniline, etc.), heteroaralkylamines (e.g. 2-, 3- or 4-pyridylmethylamine, etc.), alicyclic amines (e.g. morpholine, piperidine, piperazine, N-phenylpiperazine, 2-piperidylmethylamine, 3-(p-fluorophenylpiperazino)propylamine, etc.), and the like.

The compounds (I) thus produced via the reaction processes as depicted in Schemes A to K can be isolated and purified from the reaction mixture according to conventional methods such as, for example, evaporation of solvents, extraction by water or organic solvents, concentration, neutralization, recrystallization, distillation, column chromatography and the like, to obtain a crystalline or oily product.

The compounds (I) of the present invention can be used in the form of salts derived from pharmaceutically or physiologically acceptable acids or bases. These salts include but are not limited to the following: salts with inorganic acids such as hydrochloric acid, sulphuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases.

The starting materials (II) can be easily prepared by or according to the known techniques, for example, as disclosed in:

(1) H. Narita, Y. Konishi, J. Nitta, H. Nagaki, I. Kitayama, Y. Watanabe, and I. Saikawa, Yakugaku Zasshi, 106, 775 (1986), (2) H. Narita, Y. Konishi, J. Nitta, Y. Kobayashi, Y. Watanabe, S. Minami, and I. Saikawa, Yakugaku Zasshi, 106, 787 (1986), (3) Japanese Patent Laid Open No. 100382/1979, (4) Japanese Patent Laid Open No. 157567/1979, (5) E. E. Kilbourn, and M. C. Seidel, J. Org. Chem., 37, 1145 (1972), etc.

For example, the starting materials (II) are prepared according to the methods as illustrated in Scheme N.

pared according to methods described in known references such as, for example, A. A. Vansheidt et al., Khim. Nauka i Prom., 2, 799 (1957).

Scheme R

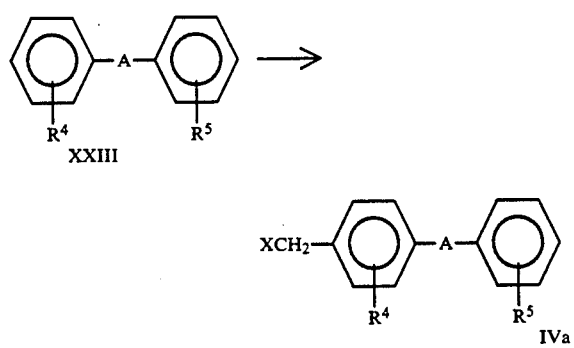

wherein each group has the above-defined meaning.

The compound (VI) wherein n is 2 (the compounds (VIb) can be prepared from the compounds (IVa) according to the methods as illustrated in Scheme S.

Scheme S

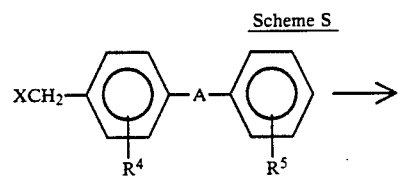

Scheme N

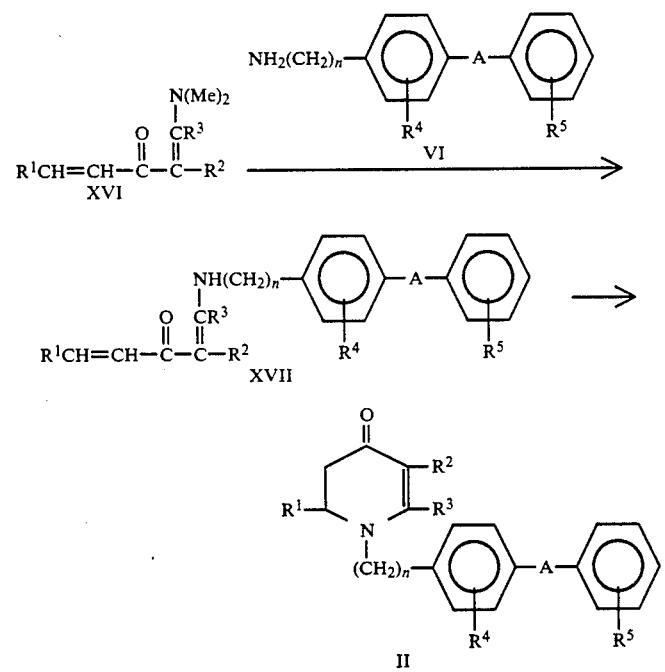

wherein each group is as defined above.

Among the starting materials and (VI), the compounds wherein n is 1 (the compounds and (VIa) are prepared by the known techniques as disclosed in Japanese Patent Laid Open No. 23868/1988, and No. 117876/1989, and European Patent Laid Open No. 0323841.

As illustrated in Scheme R, the compounds (IVa) can be easily prepared by halogenomethylation of the compounds (XXIII) commercially available or easily pre-

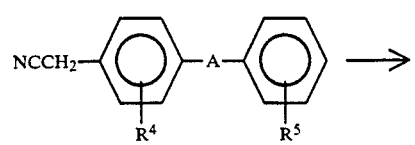

-continued
Scheme S

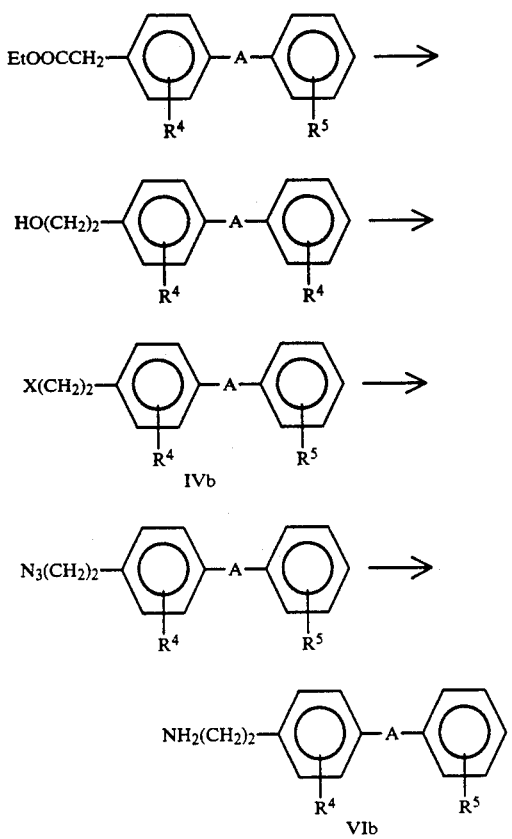

wherein each group is as defined above and X is halogen.

The compounds (I) and salts thereof according to the present invention strongly inhibit vasoconstriction and hypertension derived by angiotensin II and therefore possess potent anti-hypertensive activity in animals, more specifically mammal animals (e.g. humans, dogs, rabbits, rats, etc.). Further, the compounds (I) and salts thereof according to the present invention are of quite low toxicity and useful in treating not only hypertension but also circulatory system diseases such as heart diseases, strokes and the like.

For therapeutic use, the compounds (I) and salts thereof can be administered as pharmaceutical compositions (e.g. powders, granules, tablets, pills, capsules, injections, solutions and the like) comprising at least one such compound alone or in admixture with pharmaceutically acceptable carriers, excipients and/or diluents. The pharmaceutical compositions can be formulated in accordance with conventional methods.

Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. When used for treating adult essential hypertension, the active ingredient will preferably be administered in an appropriate amount, for example, about 10 mg to 100 mg a day orally and about 5 mg to 50 mg a day intravenously. The active ingredient will preferably be administered in equal doses two or three times a day.

The foregoing is merely illustrative of the invention and is not intended to limit the invention to the disclosed compounds.

EXAMPLES

The invention is further illustrated but in no way limited by the following reference examples, working examples, pharmaceutical examples and experimental examples.

In the specification of the present application, examples of the abbreviations used are given below. Me: Methyl, Et: Ethyl, Pr: Propyl, Bu: Butyl, iBu: Isobutyl, tBu: Tert-butyl, Ac: Acetyl, Bzo: Benzoyl, Trityl: Triphenylmethyl, Ph: Phenyl, DMF: Dimethylformamide, THF: Tetrahydrofran.

REFERENCE EXAMPLE 1

A: Ethyl 3-oxo-4-nonenate

To a solution of (3-ethoxycarbonyl-2-oxopropylidene)triphenylphosphorane (5.0 g, 12.8 mmol) in tetrahydrofuran (THF, 50 ml) were added sodium hydride (60% dispersion in oil, 1.03 g, 25.6 mmol) and then pentanal (1.10 g, 12.8 mmol) followed by stirring. After addition of water (three drops), the mixture was heated at 45° C. for 1 hour. The reaction mixture was treated with dilute hydrochloric acid and extracted with ether. The organic layer was washed with aqueous saturated sodium bicarbonate and aqueous saturated sodium chloride, dried (MgSO$_4$), and concentrated to dryness. The resulting residue was purified by column chromatography on silica gel. The column was eluted with dichloromethane-hexane (1:1 to 3:2) to give 1.02 g (40.0%) of the title compound as an oil. The $^1$H-NMR spectrum indicates that the product is a mixture of keto/enol isomers.

IR (neat): 2960, 1742, 1695, 1655, 1590 cm$^{-1}$.

$^1$H-NMR (CDCl$_3$) δ: 0.87–0.94(3H, m, (CH$_2$)$_3$CH$_3$), 1.25–1.46(7H, m, CH$_2$(CH$_2$)$_2$CH$_3$, CO$_2$CH$_2$CH$_3$), 2.53–2.69(2H, m, CH$_2$(CH$_2$)$_2$CH$_3$), 3.49(2H×7/13, s, CH$_2$CO$_2$Et), 4.20(2H, q, J=7.2Hz, CO$_2$CH$_2$CH$_3$), 5.00(1H×6/13, s, C(OH)=CHCO$_2$Et), 5.62–5.97, 6.14–6.23(2H, m, olefin-H), 12.1(1H×6/13, d, J=1.6 Hz, C(OH)=CHCO$_2$Et).

B: Ethyl 2-[(2'-t-butoxycarbonylbiphenyl-4-yl)methylaminomethylene]-3-oxo-4-nonenate A solution of ethyl 3-oxo-4-nonenate (1.00 g, 5.04 mmol) and N,N-dimethylformamide dimethyl acetal (0.94 ml, 7.08 mmol) in benzene (10 ml) was stirred at 70° C. for 1.5 hours under nitrogen stream. After cooling, a solution of 4-aminomethyl-2'-t-butoxycarbonylbiphenyl (2.86 g, ca. 10.1 mmol) in tetrahydrofuran (15 ml) was added to the reaction solution and the solution was stirred at room temperature for 2 hours and then concentrated to dryness. The resulting residue was purified by column chromatography on silica gel. The column was eluted with dichloromethane-ethyl acetate (1% to 5%) to give 1.65 g (66.6%) of the title compound as an oil.

IR (neat): 2980, 2940, 1709, 1608 cm$^{-1}$.

$^1$H-NMR (CDCl$_3$) δ: 0.87–0.94(3H, m, (CH$_2$)$_3$CH$_3$), 1.27(9H, s, CO$_2$C(CH$_3$)$_3$), 1.27–1.51(7H, m, CO$_2$CH$_2$CH$_3$, CH$_2$(CH$_2$)$_2$CH$_3$), 2.18–2.30, 2.49–2.61(2H, m, CH$_2$(CH$_2$)$_2$CH$_3$), 4.17–4.28(2H, m,

CO₂CH₂CH₃), 4.57-4.61(2H, m, CH₂Ph), 6.83-6.98, 7.27-7.54, 7.78-7.82(10H, m, olefin-H, ArH), 8.12-8.21 (1H, m, C=CHNH), 11.63(1H, br, NH).

C: Ethyl 1-[(2'-t-butoxycarbonylbiphenyl-4-yl)methyl]-6-n-butyl-4-oxo-1,4,5,6-tetrahydronicotinate A solution of ethyl 2-[(2'-t-butoxycarbonylbiphenyl-4-yl)methylaminomethylene]-3-oxo-4-nonenate (1.59 g, 3.23 mmol) in DMF (20 ml) and was heated under reflux for 4 hours. After cooling, the reaction solution was concentrated in vacuo. The resulting residue was purified by column chromatography on silica gel. The column was eluted with ethyl acetate-hexane (7:3 to 8:2) to give 1.21 g (76.2%) of the title compound as an oil.

IR (neat): 2960, 2930, 1730, 1659, 1592 cm⁻¹.

¹H-NMR (CDCl₃) δ: 0.89(3H, t, J=7.0 Hz, (CH₂)₃CH₃), 1.17-1.40 (4H, m, CH₂(CH₂)₂CH₃), 1.28(9H, s, CO₂C(CH₃)₃), 1.34 (3H, t, J=7.2 Hz, CO₂CH₂CH₃), 1.60-1.79(2H, m, CH₂(CH₂)₂CH₃), 2.38(1H, d-d, J=2.2 Hz, 16.0 Hz, C₅—H), 2.66(1H, d-d, J=6.6 Hz, 16.0 Hz, C₅—H), 3.45-3.55(1H, m, C₆—H), 4.27(2H, d-q, J=1.2 Hz, 7.2 Hz, CO₂CH₂CH₃), 4.53, 4.69(2H, 2d, J=15.2 Hz, CH₂Ph), 7.27-7.56, 7.79-7.83(8H, m, ArH), 8.28(1H, s, C₂—H).

REFERENCE EXAMPLE 2

A: Ethyl 2-[[2'-(N-methoxymethyltetrazol-5-yl)biphenyl-4-yl]methylaminomethylene-3-oxo-nonenate A solution of ethyl 3-oxo-4-nonenate (1.40 g, 7.06 mmol) and N,N-dimethylformamide dimethyl acetal (1.32 ml, 9.94 mmol) in benzene (15 ml) was stirred at 70° C. for 1.5 hours under nitrogen stream. After cooling, a solution of 5-(4'-aminomethylbiphenyl-2-yl)-N-methoxymethyltetrazole (2.72 g, ca. 9.21 mmol) in benzene (15 ml) was added to the reaction solution and the mixture was stirred at room temperature for 3 hours. After evaporation, the resulting residue was purified by flash column chromatography on silica gel. The column was eluted with dichloromethane-ethyl acetate (1% to 5%) to give 1.07 g (30.1%) of the title compound as an oil.

IR (neat): 2970, 2935, 1738, 1680, 1640, 1600, 1557 cm⁻¹.

¹H-NMR (CDCl₃) δ: 0.91(3H, t, J=7.2 Hz, (CH₂)₃CH₃), 1.23-1.50 (4H,m, CH₂(CH₂)₂CH₃), 1.32(3H, t, J=7.0 Hz, CO₂CH₂CH₃), 2.19-2.30(2H, m, CH₂(CH₂)₂CH₃), 3.32(3H, s, CH₂OCH₃), 4.23(2H, q, J=7.0 Hz, CO₂CH₂CH₃), 4.54(2H, d, J=6.2 Hz, CH₂Ar), 5.74(2H, s, CH₂OCH₃), 6.79-6.95(1H, m, olefin-H), 7.20(4H, s, Ar), 7.29-7.60, 7.88-7.93(5H, m, olefin-H, ArH), 8.15(1H, d, J=13.4 Hz, C=CHNH), 11.58 (1H, br, NH).

B: Ethyl 6-n-butyl-1-[[2'-(N-methoxymethyltetrazol-5-yl)biphenyl-4-yl]methyl]-4-oxo-1,4,5,6-tetrahydronicotinate A solution of ethyl 2-[[2'-(N-methoxymethyltetrazol-5-yl)biphenyl-4-yl]methylaminomethylene-3-oxo-nonenate (1.06 g, 2.10 mmol) in DMF (20 ml) was heated under reflux for 4 hours. After cooling, the reaction solution was concentrated in vacuo. The resulting residue was purified by flash column chromatography on silica gel. The column was eluted with ethyl acetate-hexane (8:2 to 9:1) to give 0.7 g (66.2%) of the title compound as a pale orange oil.

IR (neat): 2960, 2935, 1720, 1655, 1590 cm⁻¹.

¹H-NMR (CDCl₃) δ: 0.88(3H, t, J=6.8 Hz, (CH₂)₃CH₃), 1.21-1.37 (4H, m, CH₂(CH₂)₂CH₃), 1.34(3H, t, J=7.0 Hz, CO₂CH₂CH₃), 1.58-1.78(2H, m, CH₂(CH₂)₂CH₃), 2.39(1H, d-d, J=1.8 Hz, 16.0 Hz, C₅—H), 2.67(1H, d-d, J=6.4 Hz, 16.0 Hz, C₅—H), 3.37(3H, s, CH₂OCH₃), 3.43-3.54(1H, m, C₆—H), 4.26 (2H, d-q, J=1.2 Hz, 7.0 Hz, CO₂CH₂CH₃), 4.49, 4.63(2H, 2d, J=15.0 Hz, CH₂Ar), 5.75(2H, s, CH₂OCH₃), 7.24-7.29, 7.44-7.63, 7.90-7.94(8H, m, ArH), 8.23 (1H, s C₂—H).

The following compounds as listed in Tables 1a and 1b were prepared according to the procedure for Reference Example 2.

TABLE 1a

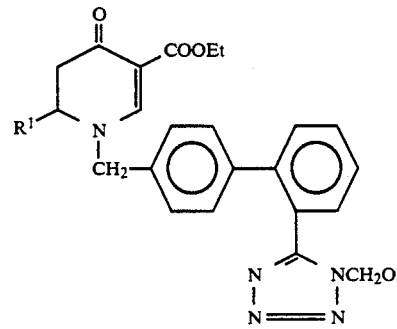

| Reference Example No. | R¹ | Appearance | IR(cm⁻¹) |
|---|---|---|---|
| 3 | CH₃(CH₂)₄ | pale yellow oil | (neat): 2930, 1730, 1680, 1653, 1587 |
| 4 | CH₃(CH₂)₂ | pale yellow oil | (neat): 2970, 1718, 1660, 1600 |
| 5 | (CH₃)₃CH(CH₂)₂ | pale orange solid | (KBr): 2950, 1720, 1655, 1590 |
| 6 | 5-methyl-2-thienyl | pale orange solid | (KBr): 2930, 1720, 1653, 1585 |

TABLE 1b

| Reference Example No. | ¹H-NMR (CDCl₃) δ |
|---|---|
| 3 | 0.87(3H, t, J=7.0Hz, (CH₂)₄CH₃), 1.20-1.40(6H, m, CH₂(CH₂)₂CH₃), 1.33(3H, t, J=7.0Hz, CO₂CH₂CH₃), 1.59-1.79(2h, m, CH₂(CH₂)₃CH₃(, 2.39(1H, d-d, J=2.0Hz, 16.0Hz, C₅—H), 2.66(1H, d-d, J=7.0Hz, 16.0Hz, C₅—H), 3.21(3H, s, CH₂OCH₃), 3.39-3.46(1H, m, C₆—H), 4.26(2H, d-q, J=1.2Hz, 7.0Hz, CO₂CH₂CH₃), 4.45, 4.59(2H, 2d, J=15.0Hz, CH₂Ar), 5.17(2H, s, CH₂OCH₃), 7.21(4H, s, ArH), 7.55-7.61, 7.66-7.75(4H, m, ArH), 8.18(1H, s, C₂—H). |
| 4 | 0.90(3H, t, J=7.0Hz, (CH₂)₂CH₃), 1.23-1.44(2H, m, CH₂CH₂CH₃), 1.33(3H, t, J=7.0Hz, CO₂CH₂CH₃), 1.52-1.75(2H, m, CH₂CH₂CH₃), 2.39(1H, d-d, J=2.0Hz, 16.2Hz, C₅—H), 2.66(1H d-d, J=7.0Hz, 16.2Hz, C₅—H), 3.2(3H, s, CH₂OCH₃), 3.37-3.47(1H, m, C₆—H), 4.26(2H, d-q, J=1.0Hz, 7.0Hz, CO₂CH₂CH₃), 4.46, 4.59(2H, 2d, J=15.4Hz, CH₂Ar), 5.17(2H, s, CH₂OCH₃), 7.21(4H, s, ArH),7.55-7.61, 7.66-7.73(4H, m, ArH), 8.18(1H, s, C₂—H). |

TABLE 1b-continued

| Reference Example No. | $^1$H-NMR (CDCl$_3$) δ |
|---|---|
| 5 | 0.86(6H, d-d, J=1.2Hz, 6.6Hz, (CH$_2$)$_2$CHC$\underline{H}_3$)$_2$), 1.05-1.36,1.43-1.75(5H, m, (CH$_2$)$_2$C$\underline{H}$(CH$_3$)$_2$), 1.34(3H, t, J=7.2Hz, CO$_2$CH$_2$C$\underline{H}_3$), 2.39(1H, d-d, J=2.2Hz, 15.8Hz, C$_5$—H), 2.67(1H, d-d, J=6.8Hz, 15.8Hz, C$_5$—H), 3.37(3H, s, CH$_2$OC$\underline{H}_3$). 3.41-3.52 (1H, m, C$_6$—H), 4.27(2H, d-q, J=1.8Hz, 7.2Hz, CO$_2$C$\underline{H}_2$CH$_3$), 4.49, 4.64(2H, 2d, J=15.2Hz, C$\underline{H}_2$Ar), 5.75(2H, s, C$\underline{H}_2$OCH$_3$), 7.20-7.29, 7.44-7.63, 7.90-7.94(8H, m, ArH), 8.24(1H, s, C$_2$—H). |
| 6 | 1.34(3H, t, J=7.2Hz, CO$_2$CH$_2$C$\underline{H}_3$), 2.44(3H, d, J=1.2Hz, ArC$\underline{H}_3$), 2.69(1H, d-d, J=4.0Hz, 16.0Hz, C$_5$—H), 2.94(1H, d-d, J=7.2Hz, 16.0Hz, C$_5$—H), 3.37(3H, s, CH$_2$OC$\underline{H}_3$), 4.28(2H, d-q, J=2.2Hz, 7.2Hz, CO$_2$CH$_2$CH$_3$). 4.48, 4.59(2H, 2d, J=15.0Hz, C$\underline{H}_2$Ar), 4.74(1H, d-d, J=4.0Hz, 7.2Hz, C$_6$—H), 5.74(2H, s, C$\underline{H}_2$OCH$_3$), 6.58(1H, d-d, J=1.2Hz, 3.4Hz, thienyl-H), 6.71(1H, d, J=3.4Hz, thienyl-H), 7.19(2H, d, J=8.6Hz, ArH(, 7.26(2H, d, J=8.6Hz, ArH), 7.44-7.62, 7.90-7.94(4H, m, ArH), 8.29(1H, s, C$_2$—H). |

WORKING EXAMPLE 1

A: Ethyl 1-[(2'-t-butoxycarbonylbiphenyl-4-yl)methyl]-6-n-butyl-4-oxo-1,4-dihydronicotinate A solution of the compound (1.39 g, 2.83 mmol) obtained in Reference Example 1C in benzene (15 ml) was heated to 80° C. under stirring and a solution of 2,3-dichloro-5,6-dicyano-1,4-benzoquinone (DDQ, 0.65 g, 2.86 mmol) in benzene (36 ml) was added dropwise to the solution over 20 minutes. After heating at 80° C. for further 30 minutes, insoluble materials were removed by filtration. The filtrate was washed with dilute aqueous sodium hydroxide and aqueous saturated sodium chloride, dried (MgSO$_4$) and concentrated in vacuo. The resulting residue was purified by flash column chromatography on silica gel. The column was eluted with chloroform-methanol (1% to 5%) to give 0.92 g (76.0%) of the title compound as a white crystal (recrystallization from ether-hexane).

mp: 80°-81° C.
IR (KBr): 2980, 1729, 1713, 1639, 1579 cm$^{-1}$.
$^1$H-NMR (CDCl$_3$) δ: 0.91(3H, t, J=7.2 Hz, (CH$_2$)$_3$C$\underline{H}_3$), 1.28(9H, s, CO$_2$C(CH$_3$)$_3$), 1.27-1.43, 1.52-1.65(4H, m, CH$_2$(C$\underline{H}_2$)$_2$CH$_3$), 1.37(3H, t, J=7.2 Hz, CO$_2$CH$_2$CH$_3$), 2.48(2H, t, J=8.0 Hz, C$\underline{H}_2$(CH$_2$)$_2$CH$_3$), 4.37(2H, q, J=7.2 Hz, CO$_2$C$\underline{H}_2$CH$_3$), 5.14 (2H, s, C$\underline{H}_2$Ar), 6.46(1H, s, C$_5$—H), 7.07-7.11, 7.27-7.56, 7.79-7.84(8H, m, ArH), 8.24(1H, s, C$_2$—H).
EI-MS m/e: 489 (M+).

| Elemental Analysis for C$_{30}$H$_{35}$NO$_5$ | | |
|---|---|---|
| C (%) | H (%) | N (%) |
| Calcd: C, 73.60; | H, 7.21; | N, 2.86 |
| Found: C, 73.63; | H, 7.12; | N, 2.97 |

B: Ethyl 6-n-butyl-1-[(2'-carboxybiphenyl-4-yl)methyl]-4-oxo-1,4-dihydronicotinate A solution of the compound (0.686 g, 1.40 mmol) obtained in Working Example 1A in a mixture of anisole (0.76 ml, 7.0 mmol) and trifluoroacetic acid (15 ml) was stirred at 0° C. for 6 hours. After evaporation in vacuo, the resulting residue was recrystallized from ether to give 0.552 g (91.0%) of the title compound as a colorless crystal.

mp: 202°-203° C.
IR (KBr): 2960, 1729, 1702, 1635, 1544 cm$^{-1}$.
$^1$H-NMR (CDCl$_3$) δ: 0.85(3H, t, J=7.2 Hz, (CH$_2$)$_3$C$\underline{H}_3$), 1.23-1.59 (4H, m, CH$_2$(C$\underline{H}_2$)$_2$CH$_3$), 1.30(3H, t, J=7.2 Hz, CO$_2$CH$_2$C$\underline{H}_3$), 2.45(2H, t, J=7.8 Hz, C$\underline{H}_2$(CH$_2$)$_2$CH$_3$), 3.50(1H, br, CO$_2$H), 4.22(2H, q, J=7.2 Hz, CO$_2$C$\underline{H}_2$CH$_3$), 5.19(2H, s, C$\underline{H}_2$Ar), 6.58(1H, s, C$_5$—H), 7.01-7.05, 7.27-7.57, 7.92-7.96(8H, m, ArH), 8.38(1H, s, C$_2$—H).

| Elemental Analysis for C$_{26}$H$_{27}$NO$_5$ | | |
|---|---|---|
| C (%) | H (%) | N (%) |
| Calcd: C, 72.04; | H, 6.28; | N, 3.23 |
| Found: C, 71.88; | H, 6.28; | N, 3.33 |

WORKING EXAMPLE 2

A: Ethyl 6-n-butyl-1-[[2'-(N-methoxymethyltetrazol-5-yl)biphenyl-4-yl]methyl]-4-oxo-1,4-dihydronicotinate A solution of the compound (0.70 g, 1.39 mmol) obtained in Reference Example 2B in benzene (10 ml) was heated to 80° C. under stirring and a solution of 2,3-dichloro-5,6-dicyano-1,4-benzoquinone (DDQ, 0.316 g, 1.39 mmol) in benzene (15 ml) was added dropwise to the solution over 20 minutes. After further heating at 80° C. for 30 minutes, insoluble materials were removed by filtration. The filtrate was washed with dilute aqueous sodium hydroxide and aqueous saturated sodium chloride, dried (MgSO$_4$) and concentrated in vacuo. The resulting residue was purified by flash column chromatography on silica gel. The column was eluted with chloroform-methanol (1% to 5%) to give 0.60 g (86.0%) of the title compound as a pale yellow powder.

IR (neat): 3430, 2960, 2940, 1725, 1690, 1631, 1575 cm$^{-1}$.
$^1$H-NMR (CDCl$_3$) δ: 0.90(3H, t, J=7.0 Hz, (CH$_2$)$_3$C$\underline{H}_3$), 1.25-1.63 (4H, m, CH$_2$(C$\underline{H}_2$)$_2$CH$_3$), 1.37(3H, t, J=7.0 Hz, CO$_2$CH$_2$C$\underline{H}_3$), 2.44(2H, t, J=7.0 Hz, C$\underline{H}_2$(CH$_2$)$_2$CH$_3$), 3.36(3H, s, CH$_2$OC$\underline{H}_3$), 4.37(2H, q, J=7.0 Hz, CO$_2$C$\underline{H}_2$CH$_3$), 5.09(2H, s, C$\underline{H}_2$Ar), 5.75(2H, s, C$\underline{H}_2$OCH$_3$), 6.44(1H, s C$_5$—H).6.99(2H, d, J=8.4 Hz, ArH), 7.24(2H, d, J=8.4 Hz, ArH), 7.41-7.59, 7.88-7.93(4H, m, ArH), 8.20(1H, s, C$_2$—H).

B: Ethyl 6-n-butyl-4-oxo-1-[[2'-(1H-tetrazol-5-yl)biphenyl-4-yl]methyl]-1,4-dihydronicotinate A solution of the compound (0.47 g, 0.937 mmol) obtained in Working Example 2A in trifluoroacetic acid (10 ml) was stirred at 50° C. for 2.5 hours. After evaporation in vacuo, the resulting residue was purified by flash column chromatography on silica gel. The column was eluted with chloroform-methanol (1% to 5%) to give 0.193 g (45.0%) of the title compound as a colorles crystal (recrystallization from ethyl acetate-ether).

mp: 119°-120° C.
IR (KBr): 2960, 1728, 1638, 1568 cm$^{-1}$.
$^1$H-NMR (CDCl$_3$) δ: 0.81(3H, t, J=7.4 Hz, (CH$_2$)$_3$C$\underline{H}_3$), 1.17-1.55 (4H, m, CH$_2$(C$\underline{H}_2$)$_2$CH$_3$), 1.30(3H, t, J=7.0 Hz, CO$_2$CH$_2$CH$_3$), 2.29(2H, t, J=7.4 Hz, CH$_2$(CH$_2$)$_2$CH$_3$), 4.15(2H, q, J=7.0 Hz, CO$_2$CH$_2$CH$_3$), 5.26(2H, s, CH$_2$Ar), 6.29(1H, s, C$_5$—H), 6.68(2H, d, J=8.0 Hz, ArH), 7.01(2H, d, J=8.0 Hz, ArH), 7.35–7.39, 7.53–7.56, 7.87–7.89(4H, m, ArH), 9.04(1H, s, C$_2$—H).

| Elemental Analysis for C$_{26}$H$_{27}$N$_5$O$_3$.0.1H$_2$O | | | |
|---|---|---|---|
| | C (%) | H (%) | N (%) |
| Calcd: | C, 67.99; | H, 5.97; | N, 15.25 |
| Found: | C, 67.83; | H, 5.93; | N, 15.11 |

The following compounds as listed in Tables 2a and 2b were prepared from the compounds obtained in Reference Examples 3–6 in the same manner as in Working Example 2.

TABLE 2a

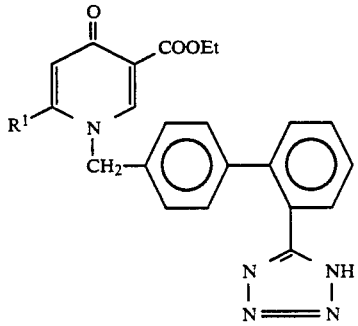

| Working Example No. | R$^1$ | mp (°C.) | IR(cm$^{-1}$) | E. Anal. (Calcd/Found) C (%), H (%), O (%) |
|---|---|---|---|---|
| 3 | CH$_3$(CH$_2$)$_4$ | 115–117 | (KBr): 2960, 1725, 1690, 1635, 1557 | C$_{27}$H$_{29}$N$_5$O$_3$.0.3H$_2$O<br>C, 67.99; H, 6.26; N, 14.68<br>C, 67.88; H, 6.12; N, 14.45 |
| 4 | CH$_3$(CH$_2$)$_2$ | 141–142 | (KBr): 2970, 1728, 1688, 1635, 1573 | C$_{25}$H$_{25}$N$_5$O$_3$.0.2H$_2$O,<br>C, 67.16; H, 5.73; N, 15.66<br>C, 66.97; H, 5.56; N, 15.66 |
| 5 | (CH$_3$)$_3$CH(CH$_2$)$_2$ | 128–129 | (KBr): 2960, 1720, 1693, 1642, 1567 | C$_{27}$H$_{29}$N$_5$O$_3$<br>C, 68.77; H, 6.20; N, 14.85<br>C, 68.70; H, 6.20; N, 15.03 |
| 6 | 5-methyl-2-thienyl | 234–236 | (KBr): 2980, 1732, 1630, 1552 | C$_{27}$H$_{23}$N$_5$O$_3$S<br>C, 65.18; H, 4.66; N, 14.07<br>C, 65.31; H, 4.65; N, 14.16 |

TABLE 2b

| Working Example No. | $^1$H-NMR (CDCl$_3$) δ |
|---|---|
| 3 | 0.80(3H, t, J=6.6Hz, (CH$_2$)$_4$CH$_3$), 1.15–1.24(3H, m, CH$_2$CH$_2$(CH$_2$)$_2$CH$_3$), 1.30(3H, t, J=7.0Hz, CO$_2$CH$_2$CH$_3$), 1.45–1.52(2H, m, CH$_2$CH$_2$(CH$_2$)$_2$CH$_3$), 2.28(2H, t, J=7.6Hz, CH$_2$(CH$_2$)$_3$CH$_3$), 4.15(2H, q, J=7.0Hz, CO$_2$ |
| 4 | 0.87(3H, t, J=7.6Hz, (CH$_2$)$_2$CH$_3$), 1.30(3H, t, J=7.0Hz, CO$_2$CH$_2$CH$_3$), 1.44–1.68(2H, m, CH$_2$CH$_2$CH$_3$), 2.27(2H, t, J=7.6Hz, CH$_2$CH$_2$CH$_3$), 4.15(2H, q, J=7.0Hz, CO$_2$CH$_2$CH$_3$), 5.2692H, s, CH$_2$Ar), 6.28(1H, s, C$_5$—H), 6.68(2H, d, J=8.4Hz, ArH), 7.01(2H, d, J=8.4Hz, ArH), 7.35–7.29, 7.53–7.58, 7.86–7.90(4H, m, ArH), 9.03(1H, s, C$_2$—H). |

TABLE 2b-continued

| Working Example No. | $^1$H-NMR (CDCl$_3$) δ |
|---|---|
| 5 | 0.78(6H, d, J=6.2Hz, (CH$_2$)$_2$CH(CH$_3$)$_2$), 1.30(3H, t, J=7.0Hz, CO$_2$CH$_2$CH$_3$), 1.33–1.58(3H, m, CH$_2$CH$_2$CH(CH$_3$)$_2$), 2.27(2H, t, J=7.6Hz, CH$_2$CH$_2$CH(CH$_3$)$_2$), 4.15(2H, q, J=7.0Hz, CO$_2$CH$_2$CH$_3$), 5.26(2H, s, CH$_2$Ar), 6.28(1H, s, C$_5$—H), 6.68(2H, d, J=8.4Hz, ArH), 7.01(2H, d, J=8.4Hz, ArH), 7.34–7.38, 7.50–7.56, 7.86–7.91(4H, m, ArH), 9.04(1H, s, C$_2$—H). |
| 6 | 1.28(3H, t, J=7.0Hz, CO$_2$CH$_2$CH$_3$), 2.43(3H, s, ArCH$_3$), 4.14(2H, q, J=7.0Hz, CO$_2$CH$_2$CH$_3$), 5.23(2H, s, CH$_2$Ar), 6.47(1H, s, C$_5$—H), 6.52(1H, d, J=3.6Hz, thienyl-H), 6.61(1H, d-d, J=1.0Hz, 3.6Hz, thienyl-H), 6.74(2H, d, J=8.2Hz, ArH), 7.06(2H, d, J=8.2Hz, ArH), 7.40–7.62, 7.84–7.88(4H, m, ArH), 8.98((1H, s, C$_2$—H). |

REFERENCE EXAMPLE 7

A: 2-n-Butyl-4-hydroxy-6-chloromethylpyrimidine

To a solution of valerylamidine hydrochloride (3.06 g, 2.2 mmol) and methyl 4-chloroacetoacetate (2.9 ml, 2.5 mmol) in methanol (20 ml) under ice-cooling was added a solution of sodium methoxide prepared from sodium (1.14 g) and methanol (15 ml) and the mixture was stirred for 8 hours. After the mixture was heated under reflux for an additional 8 hours, insoluble materials were removed by filtration and the filtrate was concentrated to dryness in vacuo. The resulting residue was purified by column chromatography on silica gel. The column was eluted with ethyl acetate-hexane (3:2) to give 1.66 g (37%) of the title compound as a white crystal.

mp: 102°–104° C.

| Elemental Analysis for $C_9H_{13}ClN_2O$ | | |
|---|---|---|
| C (%) | H (%) | N (%) |
| Calcd: C, 53.87; | H, 6.53; | N, 13.96 |
| Found: C, 54.07; | H, 6.56; | N, 13.74 |

IR (KBr): 1660, 1610, 1570 cm$^{-1}$.

$^1$H-NMR (CDCl$_3$) δ: 0.96(3H, t, J=7.2 Hz), 1.40(2H, m), 1.77(2H, m), 2.69(2H, t, J=7.6 Hz), 4.39(2H, s), 6.54(1H, s).

B: 2-n-Butyl-4-hydroxy-6-methoxymethylpyrimidine

To a solution of the compound (1.01 g, 0.50 mmol) prepared in Reference Example 7A in methanol (15 ml) were added a solution of sodium methoxide prepared from sodium (250 mg, 1.1 mmol) and methanol (5 ml) and the mixture was heated under reflux for 2 days. After insoluble materials were removed by filtration, the filtrate was concentrated to dryness in vacuo. The resulting residue was purified by column chromatography on silica gel. The column was eluted with ethyl acetate-hexane (2:1) to give 830 mg (84%) of the title compound as a white crystal.

mp: 96°-98° C.

| Elemental Analysis for $C_{10}H_{16}N_2O_2$ | | |
|---|---|---|
| C (%) | H (%) | N (%) |
| Calcd: C, 61.20; | H, 8.22; | N, 14.27 |
| Found: C, 60.97; | H, 8.28; | N, 14.09 |

IR (KBr): 1685, 1605, 1570 cm$^{-1}$.

$^1$H-NMR (CDCl$_3$) δ: 0.95(3H, t, J=7.4 Hz), 1.40(2H, m), 1.76(2H, m), 2.68(2H, t, J=7.4 Hz), 3.48(3H, s), 4.32(2H, s), 6.45(1H, s).

REFERENCE EXAMPLE 8

Ethyl 2-n-butyl-4-hydroxypyrimidine-5-carboxylate

To a mixture of valerylamidine hydrochloride (5.1 g, 37 mmol) in ethanol (30 ml) was added a solution of sodium ethoxide prepared from sodium (1,9 g, 83 mmol) and ethanol (30 ml) under ice-cooling and the mixture was stirred. White precipitates were removed by filtration and the filtrate was then added dropwise to a solution of diethyl ethoxymethylenemalonate (8.0 g, 37 mmol) in ethanol (20 ml) under ice-cooling. After stirring for 20 minutes, the mixture was heated at 60° C. for 40 minutes. After cooling, the reaction mixture was neutralized with 4.7N hydrochloric acid, and extracted with ethyl acetate. The organic layer was washed with water, dried (MgSO$_4$), and concentrated to dryness in vacuo. The resulting pale yellow solids were washed with ether-hexane and dried to give 5.5 g (66%) of the title compound as a colorless crystal.

mp: 111°-114° C.

IR (KBr): 1750, 1705, 1680, 1580, 1570, 1495 cm$^{-1}$.

$^1$H-NMR (CDCl$_3$) δ: 0.96(3H, t, J=7.4 Hz), 1.38(3H, t, J=7.2 Hz), 1.3-1.5(2H, m), 1.7-1.9(2H, m), 2.80(2H, t, J=7.8 Hz), 4.38(2H, q, J=7.2, 14.4 Hz), 8.74(1H, s).

REFERENCE EXAMPLE 9

2-n-Butyl-4-hydroxy-5-nitropyrimidine

To a solution of valerylamidine hydrochloride (10 g, 7.3 mmol) in ethanol (10 ml) under ice-cooling was added a solution of sodium ethoxide prepared from sodium (3.6 g, 16.1 mmol) and ethanol (70 ml) and white precipitates were removed by filtration. The filtrate which was then added dropwise to a solution of ethyl ethoxymethylenenitroacetate (J. Heterocyclic Chem., 22, 337 (1985), 13.8 g, 7.3 mmol) in ethanol (30 ml) under ice-cooling. After stirring for 20 minutes, the mixture was heated at 50° C. for 30 minutes, neutralized with 4.7N hydrochloric acid, and concentrated to dryness in vacuo. The resulting residue was treated with ethyl acetate-water and the organic layer was washed with aqueous saturated sodium chloride, dried (MgSO$_4$), and evaporated to dryness in vacuo. The resulting residue was purified by flash column chromatography on silica gel. The column was eluted with ethyl acetate-hexane (2:1 to 4:1) to give 2.18 g (15%) of the title compound as a pale yellow crystal (recrystallization from ether-hexane).

mp: 67°-69° C.

| Elemental Analysis for $C_8H_{11}N_3O_3$ | | |
|---|---|---|
| C (%) | H (%) | N (%) |
| Calcd: C, 48.73; | H, 5.62; | N, 21.31 |
| Found: C, 48.50; | H, 5.68; | N, 21.11 |

IR (KBr): 1690, 1560, 1530, 1480, 1335 cm$^{-1}$.

$^1$H-NMR (CDCl$_3$) δ: 0.98(3H, t, J=7.2 Hz), 1.3-1.6(2H, m), 1.7-1.9 (2H, m), 2.85(2H, t, J=7.6 Hz), 9.00(1H, s).

REFERENCE EXAMPLE 10

2-n-Butyl-4-hydroxy-6-methoxycarbonylmethylpyrimidine

To a solution of dimethyl 3-ketoglutarate (9.7 g, 56 mmol) and valerylamidine hydrochloride (7.6 g, 56 mmol) in methanol (20 ml) under ice-cooling was added a solution of sodium methoxide (Na 2.7 g, 0.12 mmol, MeOH 40 ml) and the mixture was stirred for 14 hours. After the mixture was heated under reflux for an additional 6 hours, insoluble materials were removed by filtration and the filtrate was concentrated to dryness in vacuo. The resulting residue was purified by flash column chromatography on silica gel. The column was eluted with ethyl acetate-hexane (2:1) and then ethyl acetate-methanol (4:1) to give 5.0 g (40%) of the title compound as a white needle.

mp: 83°-85° C.

| Elemental Analysis for $C_{11}H_{16}N_2O_3$ | | |
|---|---|---|
| C (%) | H (%) | N (%) |
| Calcd: C, 58.91; | H, 7.19; | N, 12.49 |
| Found: C, 58.95; | H, 7.20; | N, 12.51 |

IR (KBr): 1740, 1680, 1650, 1610 cm$^{-1}$.

$^1$H-NMR (CDCl$_3$) δ: 0.94(3H, t, J=7.2 Hz), 1.3-1.5(2H, m), 1.6-1.9 (2H, m), 3.59(2H, s), 3.74(3H, s), 6.30(1H, s).

WORKING EXAMPLE 7

2-n-Butyl-3-[(2'-cyanobiphenyl-4-yl)methyl]-6-methoxymethyl-4(3H)-pyrimidone

To a solution of the compound (200 mg, 1.0 mmol) obtained in Reference Example 7B in tetrahydrofuran (15 ml) were added sodium hydride (60% dispersion in oil, 45 mg, 1.1 mmol) and 4-(2'-cyanophenyl)benzyl bromide (280 mg, 1.0 mmol) and the mixture was stirred at 70° C. for 3 days. After removal of insoluble materials by filtration, the filtrate was concentrated to dryness in vacuo. The resulting residue was purified by flash column chromatography on silica gel. The column was eluted with ethyl acetate-hexane (2:1) to give 175 mg (44%) of the title compound as an oil.

IR (neat): 2210, 1680, 1600, 1540 cm$^{-1}$.

$^1$H-NMR (CDCl$_3$) δ: 0.90(3H, t, J=7.0 Hz), 1.37(2H, m), 1.67(2H, m), 2.70(2H, t, J=7.4 Hz), 3.50(3H, s), 4.32(2H, s), 5.38(2H, s), 6.56(1H, s), 7.30(2H, d, J=8.0 Hz), 7.4–7.8(6H, m).

WORKING EXAMPLE 8

2-n-Butyl-3-[[2′-(1H-tetrazol-5-yl)biphenyl-4-yl]methyl]-6-methoxymethyl-4(3H)-pyrimidone A solution of the compound (780 mg, 2.0 mmol) obtained in Working Example 7, sodium azide (1.3 g, 20 mmol) and ammonium chloride (1.08 g, 20 mmol) in DMF (30 ml) was stirred at 110° C. for 3 days. Additional sodium azide (650 mg) and ammonium chloride (500 mg) were added to the mixture which was stirred at 110° C. for 3 days. The reaction mixture was poured into water, and extracted with ethyl acetate. The organic layer was washed with dilute hydrochloric acid, water, dried (MgSO$_4$), and concentrated to dryness in vacuo. The resulting pale yellow solids were washed with ethyl acetate-hexane, and dried to give 467 mg (53%) of the title compound as a colorless crystal.

mp: 194°–197° C.

| Elemental Analysis for C$_{24}$H$_{26}$N$_6$O$_2$ | | |
|---|---|---|
| C (%) | H (%) | N (%) |
| Calcd: C, 66.99; | H, 6.06; | N, 19.52 |
| Found: C, 67.11; | H, 6.18; | N, 19.27 |

IR (KBr): 1650, 1540 cm$^{-1}$.

$^1$H-NMR (d$_6$-DMSO) δ: 0.80(3H, t, J=7.2 Hz), 1.25(2H, m), 1.53 (2H, m), 2.63(2H, t, J=7.4 Hz), 3.94(3H, s), 4.25(2H, s), 5.29(2H, s), 6.29(1H, s), 7.09(4H, s), 7.5–7.7(4H, m).

WORKING EXAMPLE 9

Ethyl 2-n-butyl-4-oxo-3-[[2′-(N-triphenylmethyltetrazol-5-yl)biphenyl-4-yl]methyl]-3,4-dihydropyrimidine-5-carboxylate (9A) and ethyl 2-n-butyl-4-oxo-1-[[2′-(N-triphenylmethyltetrazol-5-yl)biphenyl-4-yl]methyl]-1,4-dihydropyrimidine-5-carboxylate (9B)

To a solution of the compound (240 mg, 1.1 mmol) obtained in Reference Example 8 in tetrahydrofuran (30 ml) were added sodium hydride (60% dispersion in oil, 47 mg, 1.2 mmol) and 4-[2′-(N-triphenylmethyltetrazol-5-yl)phenyl]benzyl bromide (600 mg, 1.1 mmol) and the mixture was stirred at 70° C. for 4 days. After removal of insoluble materials by filtration, the filtrate was concentrated to dryness in vacuo. The resulting residue was purified by flash column chromatography on silica gel. The column was eluted with ethyl acetate-hexane (2:3) and then chloroform-methanol (10:1) to obtain 310 mg (41%) of the title compound (9A) as a white powder and 70 mg (9.3%) of the title compound (9B) as a pale yellow powder.

9A

IR (KBr): 1740, 1705, 1680, 1580, 1515 cm$^{-1}$.

$^1$H-NMR (CDCl$_3$) δ: 0.86(3H, t, J=7.2 Hz), 1.2–1.3(2H, m), 1.39 (3H, t, J=7.2 Hz), 1.5–1.7(2H, m), 2.63(2H, t, J=7.4 Hz), 4.39(2H, q, J=7.2, 14.0 Hz), 5.24(2H, s), 6.9–7.5(22H, m), 7.9–8.0(1H, m), 8.63(1H, s).

9B

IR (KBr): 1735, 1700, 1640, 1520 cm$^{-1}$.

$^1$H-NMR (CDCl$_3$) δ: 0.85(3H, t, J=7.4 Hz), 1.2–1.3(2H, m), 1.36 (3H, t, J=7.0 Hz), 1.6–1.8(2H, m), 2.52(2H, t, J=7.8 Hz), 4.32(2H, q, J=7.0, 14.2 Hz), 4.93(2H, s), 6.8–7.5(22H, m), 7.9–8.0(1H, m), 8.01(1H, s).

WORKING EXAMPLE 10

Ethyl 2-n-butyl-4-oxo-3-[[2′-(1H-tetrazol-5-yl)biphenyl-4-yl]methyl]-3,4-dihydropyrimidine-5-carboxylate A solution of the compound (9A, 310 mg, 0.44 mmol) obtained in Working Example 9 in a mixture of trifluoroacetic acid (8 ml) and water (8 ml) was stirred at room temperature for 6 hours. To the reaction mixture was added chloroform and the organic layer was washed with water, dried (MgSO$_4$), and evaporated to dryness in vacuo. The resulting residue was purified by flash column chromatography on silica gel. The column was eluted with chloroform-methanol (20:1) to obtain 127 mg (62%) of the title compound as a pale yellow crystal.

mp: 168°–173° C.

IR (KBr): 1725, 1655, 1520 cm$^{-1}$.

$^1$H-NMR (d$_6$-DMSO) δ: 0.81(3H, t, J=7.0 Hz), 1.2–1.3(2H, m), 1.27 (3H, t, J=7.0 Hz), 1.5–1.6(2H, m), 2.72(2H, t, J=7.0 Hz), 4.24(2H, q, J=7.0, 14.2 Hz), 5.32(2H, s), 7.0–7.1(4H, m), 7.5–7.7(4H, m), 8.52(1H, s).

WORKING EXAMPLE 11

Ethyl 2-n-butyl-4-oxo-1-[[2′-(1H-tetrazol-5-yl)biphenyl-4-yl]methyl]-1,4-dihydropyrimidine-5-carboxylate The title compound was obtained as pale yellow powder (12 mg, 26%) from the compound (9B, 70 mg, 0.10 mmol) prepared in Working Example 9 according to the procedure for Working Example 10.

IR (KBr): 1730, 1635, 1615, 1515 cm$^{-1}$.

$^1$H-NMR (CD$_3$OD) δ: 0.88(3H, t, J=7.2 Hz), 1.3–1.4(2H, m), 1.36 (3H, t, J=7.0 Hz), 1.5–1.7(2H, m), 2.70(2H, t, J=7.8 Hz), 4.37(2H, q, J=7.0, 14.2 Hz), 5.39(2H, s), 7.1–7.3(4H, m), 7.5–7.7(4H, m), 8.74(1H, s).

WORKING EXAMPLE 12

2-n-Butyl-5-nitro-3-[[2′-(N-triphenylmethyltetrazol-5-yl)biphenyl-4-yl]methyl]-4(3H)-pyrimidone (6A) and 2-n-butyl-5-nitro-1-[[2′-(N-triphenylmethyltetrazol-5-yl)biphenyl-4-yl]methyl]-4(1H)pyrimidone (6B)

To a solution of the compound (300 mg, 1.5 mmol) obtained in Reference Example 9 in DMF (10 ml) were added sodium hydride (60% dispersion in oil, 67 mg, 1.7 mmol) and 4-[2′-(N-triphenylmethyltetrazol-5-yl)phenyl]benzyl bromide (860 mg, 1.5 mmol) and the mixture was stirred at 80° C. for 1 hour. After cooling, the reaction mixture was poured into water and extracted with ethyl acetate. The organic layer was washed with water, dried (MgSO$_4$), and concentrated to dryness. The resulting residue was purified by flash column chromatography on silica gel. The column was eluted with ethyl acetate-hexane (initially 1:3, then 1:1, and finally 3:1) to obtain 77 mg (7.5%) of the title compound (12A) as a pale yellow powder and 70 mg (6.8%) of the title compound (12B) as a pale orange powder.

12A

IR (KBr): 1705, 1580, 1510, 1445, 1330 cm$^{-1}$.

$^1$H-NMR (CDCl$_3$) δ: 0.88(3H, t, J=7.2 Hz), 1.2-1.4(2H, m), 1.5-1.8 (2H, m), 2.71(2H, t, J=7.4 Hz), 5.28(2H, s), 6.8-7.6 (22H, m), 7.9-8.0(1H, m), 8.87(1H, s).

12B

IR (KBr): 1680, 1640, 1510, 1440 cm$^{-1}$.

$^1$H-NMR (d$_6$-DMSO) δ: 0.73(3H, t, J=7.0 Hz), 1.0-1.3(2H, m), 1.3-1.5(2H, m), 2.52(2H, t, J=7.8 Hz), 5.35(2H, s), 6.8-7.9(23H, m), 9.23(1H, s).

WORKING EXAMPLE 13

2-n-Butyl-5-nitro-3-[[2'-(1H-tetrazol-5-yl)biphenyl-4-yl]methyl]-4(3H)-pyrimidone The title compound was obtained as pale yellow powder (19 mg, 42%) from the compound (12A, 77 mg, 0.11 mmol) prepared in Working Example 12 according to the procedure for Working Example 10.

IR (KBr): 1700, 1515, 1335 cm$^{-1}$.

$^1$H-NMR (CD$_3$Cl$_3$) δ: 0.91(3H, t, J=7.0 Hz), 1.3-1.5(2H, m), 1.6-1.9(2H, m), 2.85(2H, t, J=7.6 Hz), 5.32(2H, s), 7.0-7.7(7H, m), 7.90(2H, d, J=6.8 Hz), 8.90(1H, s).

WORKING EXAMPLE 14

2-n-Butyl-5-nitro-1-[[2'-(1H-tetrazol-5-yl)biphenyl-4-yl]methyl]-4(1H)-pyrimidone The title compound was obtained as pale yellow powder (12 mg, 24%) from the compound (12B, 70 mg, 0.10 mmol) prepared in Working Example 12 according to the procedure for Working Example 10.

IR (KBr): 1660, 1510, 1480, 1450 cm$^{-1}$.

$^1$H-NMR (CD$_3$OD) δ: 0.88(3H, t, J=7.0 Hz), 1.2-1.5(2H, m), 1.5-1.7(2H, m), 2.71(2H, t, J=7.4 Hz), 5.41(2H, s), 7.2-7.8(8H, m), 9.15(1H, s).

WORKING EXAMPLE 15

2-n-Butyl-6-methoxycarbonylmethyl-3-[[2'-(N-triphenylmethyltetrazol-5-yl)biphenyl-4-yl]methyl]-4(3H)-pyrimidone A mixture of the compound (0.8 g, 3.6 mmol) obtained in Reference Example 10, 4-[2'-(N-triphenylmethyltetrazol-5-yl)phenyl]benzyl bromide (2.0 g, 3.6 mmol) and sodium hydride (60% dispersion in oil, 160 mg, 3.9 mmol) in tetrahydrofuran (60 ml) was heated under reflux for 5 days. After cooling, insoluble materials were removed by filtration and the filtrate was concentrated to dryness in vacuo. The resulting residue was purified by flash column chromatography on silica gel. The column was eluted with ethyl acetate-hexane (initially 1:3, then 1:1 and finally 3:1) to give 298 mg (11%) of the title compound as a pale yellow powder.

IR (KBr): 1740, 1680, 1600, 1540 cm$^{-1}$.

$^1$H-NMR (CDCl$_3$) δ: 0.84(3H, t, J=7.2 Hz), 1.2-1.4(2H, m), 1.5-1.7(2H, m), 2.55(2H, t, J=7.0 Hz), 3.56(2H, s), 3.74(3H, s), 5.18(2H, s), 6.39(1H, s), 6.8-7.5(22H, m), 7.9-8.0(1H, m).

WORKING EXAMPLE 16

2-n-Butyl-6-methoxycarbonylmethyl-3-[[2'-(1H-tetrazol-5-yl)biphenyl-4-yl]methyl]-4(3H)-pyrimidone The title compound was obtained as pale yellow powder (120 mg, 63%) from the compound (290 mg, 0.41 mmol) prepared in Working Example 15 according to the procedure for Working Example 10.

mp: 210°-214° C.

| Elemental Analysis for C$_{25}$H$_{25}$N$_6$O$_3$.1.3H$_2$O | | |
|---|---|---|
| C (%) | H (%) | N (%) |
| Calcd: C, 62.44; | H, 5.78; | N, 17.47 |
| Found: C, 62.84; | H, 5.63; | N, 17.00 |

IR (KBr): 1740, 1640, 1535 cm$^{-1}$.

$^1$H-NMR (DMSO-d$_6$) δ: 0.79(3H, t, J=7.2 Hz), 1.1-1.4(2H, m), 1.4-1.6(2H, m), 2.63(2H, t, J=7.8 Hz), 3.60(2H, s), 3.64(3H, s), 5.27(2H, s), 6.37(1H, s), 7.09(4H, s), 7.5-7.7(4H, m).

REFERENCE EXAMPLE 11

2-n-Butyl-4H-3,1-benzoxazin-4-one

A mixture of anthranilic acid (2.0 g, 14.6 mmol) and valerianic acid anhydride (6.0 ml, 30.3 mmol) was heated at 180° C. for 2 hours. After cooling, the reaction mixture was concentrated in vacuo. The resulting residue was purified by flash column chromatography on silica gel. The column was eluted with dichloromethane-hexane (1:1~7:3) to give 2.47 g (83.3%) of the title compound as a pale yellow oil.

IR (neat): 2960, 1758, 1642, 1610 cm$^{-1}$.

$^1$H-NMR (CDCl$_3$) δ: 0.97(3H, t, J=7.2 Hz, (CH$_2$)$_3$CH$_3$), 1.37-1.55 (2H, m, (CH$_2$)$_2$CH$_2$CH$_3$), 1.75-1.90(2H, m, CH$_2$CH$_2$CH$_2$CH$_3$), 2.70(2H, t, J=7.2 Hz, CH$_2$(CH$_2$)$_2$CH$_3$), 7.46-7.59, 7.76-7.85, 8.18-8.22(4H, m, ArH).

The following compounds as listed in Tables 3a and 3b were prepared in the same manner as in Reference Example 11.

TABLE 3a

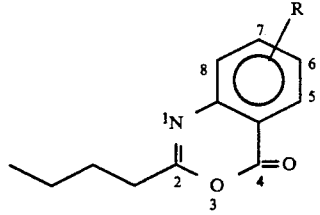

| Reference Example No. | R | Appearance mp (°C.) | IR(cm$^{-1}$) |
|---|---|---|---|
| 12 | 7-NO$_2$ | pale yellow crystal | (KBr): 2965, 1763, 1642, 1614, 1538, 1350 |
| 13 | 7-Cl | pale yellow solid | (CHCl$_3$): 2935, 1750, 1633, 1595 |
| 14 | 5-CH$_3$ | colorless plate 44-44.5 | (KBr): 2955, 1760, 1748, 1644, 1595, 1570 |
| | | Elemental Analysis C$_{13}$H$_{15}$NO$_2$ | |
| | | C (%), H (%), O (%) | |
| | | Calcd: C, 71.87; H, 6.96; N, 6.45 | |
| | | Found: C, 71.94; H, 7.09; N, 6.47 | |
| 15 | 6-Cl | pale yellow solid | (KBr): 2950, 1761, 1642, 1600, 1470 |
| 16 | 6-O—CO-n-Bu | pale yellow | (KBr): 2960, 1758, |

TABLE 3a-continued

![structure]

| Reference Example No. | R | Appearance mp (°C.) | IR(cm⁻¹) |
|---|---|---|---|
| | | solid | 1650, 1610 |

TABLE 3b

| Reference Example No. | ¹H-NMR (CDCl₃) δ |
|---|---|
| 12 | 0.99(3H, t, J=7.2Hz, (CH₂)₃CH₃), 1.38-1.56(2H, m, (CH₂)₂CH₂CH₃), 1.76-1.92(2H, m, CH₂CH₂CH₂CH₃), 2.75(2H, t, J=7.2Hz, CH₂(CH₂)₂CH₃), 8.27(1H, d-d, J=2.2Hz, 8.8Hz, ArH), 8.38(1H, d, J=8.8Hz, ArH), 8.40(1H, d, J=2.2Hz, ArH). |
| 13 | 0.97(3H, t, J=7.2Hz, (CH₂)₃CH₃), 1.36-1.54(2H, m, (CH₂)₂CH₂CH₃), 1.73-1.88(2H, m, CH₂CH₂CH₂CH₃), 2.69(2H, t, J=7.4Hz, CH₂(CH₂)₂CH₃), 7.45(1H, d-d, J=2.0Hz, 8.4Hz, ArH), 7.57(1H, d, J=2.0Hz, ArH), 8.11(1H, d, J=8.4Hz, ArH). |
| 14 | 0.97(3H, t, J=7.4Hz, (CH₂)₃CH₃), 1.36-1.54(2H, m, (CH₂)₂CH₂CH₃), 1.73-1.88(2H, m, CH₂CH₂CH₂CH₃), 2.66(2H, t, J=7.4Hz, CH₂(CH₂)₂CH₃), 2.80(3H, s, ArCH₃), 7.25-7.29, 7.36-7.40, 7.58-7.66(3H, m, ArH). |
| 15 | 0.97(3H, t, J=7.2Hz, (CH₂)₃CH₃), 1.36-1.54(2H, m, (CH₂)₂CH₂CH₃), 1.73-1.88(2H, m, CH₂CH₂CH₂CH₃), 2.69(2H, t, J=7.2Hz, CH₂(CH₂)₂CH₃), 7.51(1H, d, J=8.6Hz, ArH), 7.73(1H, d-d, J=2.4Hz, 8.6Hz, ArH), 8.15(1H, d, J=2.4Hz, ArH). |
| 16 | 0.97(3H, t, J=7.2Hz, (CH₂)₃CH₃), 0.98(3H, t, J=7.2Hz, (CH₂)₃CH₃), 1.35-1.56(4H, m, (CH₂)₂CH₂CH₃ × 2), 1.69-1.89(4H, m, CH₂CH₂CH₂CH₃ × 2), 2.61(2H, t, J=7.6Hz, CH₂(CH₂)₂CH₃), 2.70(2H, t, J=7.2Hz, CH₂(CH₂)₂CH₃), 7.51(1H, d-d, J=2.6Hz, 8.8Hz, ArH), 7.60(1H, d, J=8.89Hz, ArH), 7.89(1H, d, J=2.6Hz, ArH). |

WORKING EXAMPLE 17

6-n-Butyl-3-[[2'-(N-methoxymethyltetrazol-5-yl)biphenyl-4-yl]methyl]-4(3H)-quinazolinone A mixture of 6-n-butyl-4H-3,1-benzoxazin-4-one (1.4 g, 6.89 mmol) and 5-(4'-aminomethylbiphenyl-2-yl)-N-methoxymethyltetrazole (2.85 g, ca. 9.65 mmol) in xylene (50 ml) was heated under reflux for 8 hours while water was removed by a Dean-Stark trap. After cooling, the reaction mixture was concentrated in vacuo. The resulting residue was purified by flash column chromatography on silica gel. The column was eluted with chloroform-ethyl acetate (1% to 10%) to give 1.44 g (43.6%) of the title compound as a colorless crystal. mp: 112°-112.5° C.

IR(KBr): 2965, 1673, 1598, 1572 cm⁻¹.

¹H-NMR (CDCl₃) δ: 0.92(3H, t, J=7.2 Hz, (CH₂)₃CH₃), 1.32-1.51 (2H, m, (CH₂)₂CH₂CH₃), 1.69-1.84(2H, m, CH₂CH₂CH₂CH₃), 2.70(2H, t, J=7.6 Hz, CH₂(CH₂)₂CH₃), 3.12(3H, s, CH₂OCH₃), 5.03(2H, s, CH₂OCH₃), 5.37(2H, s, CH₂Ar), 7.11(4H, s, ArH), 7.42-7.79, 8.26-8.31(8H, m, ArH).

| Elemental Analysis for C₂₈H₂₈N₆O₂ | | | |
|---|---|---|---|
| | C (%) | H (%) | N (%) |
| Calcd: | C, 69.98; | H, 5.87; | N, 17.49 |
| Found: | C, 69.81; | H, 5.81; | N, 17.42 |

The following compounds as listed in Tables 4a and 4b were prepared from the compounds obtained in Reference Examples 12-16 in the same manner as in Working Example 17.

TABLE 4a

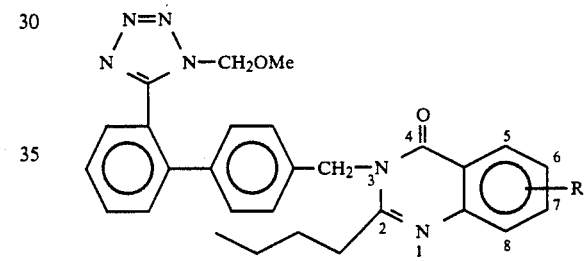

| Working Example No. | R | Appearance | IR(KBr, cm⁻¹) |
|---|---|---|---|
| 18 | 7-NO₂ | pale yellow powder | 2960, 1680, 1593, 1530, 1465, 1340 |
| 19 | 7-Cl | white powder | 2940, 1677, 1590, 1562 |
| 20 | 5-CH₃ | white powder | 2960, 1667, 1598, 1568 |
| 21 | 6-Cl | pale red powder | 2955, 1672, 1588, 1561 |
| 22a | 6-O—CO-n-Bu | pale red powder | 2955, 1752, 1670, 1595 |
| 22b | 5-COOMe | pale yellow solid | 2960, 1732, 1673, 1595, 1580 |

TABLE 4b

| Working Example No. | ¹H-NMR (CDCl₃) δ |
|---|---|
| 18 | 0.94(3H, t, J=7.0Hz, (CH₂)₃CH₃), 1.33-1.51(2H, m, (CH₂)₂CH₂CH₃), 1.72-1.87(2H, m, CH₂CH₂CH₂CH₃), 2.75 (2H, t, J=7.2Hz, CH₂(CH₂)₂CH₃), 3.14(3H, s, CH₂OCH₃), 5.07(2H, s, CH₂OCH₃), 5.37(2H, s, CH₂Ar), 7.08-7.17, 7.50-7.56, 7.58-7.71(8H, m, ArH), 8.21(1H, d-d, J=2.2Hz, 8.8Hz, ArH), 8.44(1H, d, J=8.8Hz, ArH), 8.52(1H, d, J=2.2Hz, ArH) |

TABLE 4b-continued

| Working Example No. | $^1$H-NMR (CDCl$_3$) δ |
|---|---|
| 19 | 0.92(3H, t, J=7.2Hz, (CH$_2$)$_3$CH$_3$), 1.31–1.49(2H, m, (CH$_2$)$_2$CH$_2$CH$_3$), 1.67–1.83(2H, m, CH$_2$CH$_2$CH$_2$CH$_3$), 2.69 (2H, t, J=7.6Hz, CH$_2$(CH$_2$)$_2$CH$_3$), 3.13(3H, s, CH$_2$OCH$_3$), 5.04(2H, s, CH$_2$OCH$_3$), 5.34(2H, s, CH$_2$Ar), 7.06–7.15, (4H, m, ArH), 7.41(1H, d-d, J=2.0Hz, 8.6Hz, ArH), 7.50–7.58, 7.62–7.70(5H, m, ArH), 8.21(1H, d, J=8.6Hz, ArH) |
| 20 | 0.92(3H, t, J=7.2Hz, (CH$_2$)$_3$CH$_3$), 1.31–1.50(2H, m, (CH$_2$)$_2$CH$_2$CH$_3$), 1.67–1.83(2H, m, CH$_2$CH$_2$CH$_2$CH$_3$), 2.67 (2H, t, J=7.6Hz, CH$_2$(CH$_2$)$_2$CH$_3$), 2.86(3H, s, ArCH$_3$), 3.11 (3H, s, CH$_2$OCH$_3$), 5.02(2H, s, CH$_2$OCH$_3$), 5.31(2H, s, CH$_2$Ar), 7.10(4H, s, ArH), 7.18–7.23, 7.47–7.70(7H, m, ArH) |
| 21 | 0.92(3H, t, J=7.2Hz, (CH$_2$)$_3$CH$_3$), 1.30–1.50(2H, m, (CH$_2$)$_2$CH$_2$CH$_3$), 1.68–1.83(2H, m, CH$_2$CH$_2$CH$_2$CH$_3$), 2.69 (2H, t, J=7.6Hz, CH$_2$(CH$_2$)$_2$CH$_3$), 3.13(3H, s, CH$_2$OCH$_3$), 5.04(2H, s, CH$_2$OCH$_3$), 5.35(2H, s, CH$_2$Ar), 7.05–7.15 (4H, m, ArH), 7.48–7.71(6H, m, ArH), 8.24(1H, d, J=2.2Hz, ArH) |
| 22a | 0.93(3H, t, J=7.4Hz, (CH$_2$)$_3$CH$_3$), 0.98(3H, t, J=7.2Hz, (CH$_2$)$_3$CH$_3$), 1.33–1.56(4H, m, CH$_2$)$_2$CH$_2$CH$_3$×2), 1.69–1.84(4H, m, CH$_2$CH$_2$CH$_2$CH$_3$×2), 2.61(2H, t, J=7.4Hz, CH$_2$(CH$_2$)$_2$CH$_3$), 2.75(2H, t, J=7.4Hz, CH$_2$(CH$_2$)$_2$CH$_3$), 3.28 (3H, s, CH$_2$OCH$_3$), 5.40(2H, s, CH$_2$Ar), 5.71(2H, s, CH$_2$OCH$_3$), 7.09(2H, d, J=8.4Hz, ArH), 7.17(2H, d, J=8.4Hz, ArH), 7.40–7.60 (4H, m, ArH), 7.69(1H, d, J=9.0Hz, ArH), 7.88(1H, d-d, J=2.4Hz, 6.8Hz, ArH), 7.96(1H, d, J=2.6Hz, ArH) |
| 22b | 0.92(3H, t), 1.30–1.48(2H, m), 1.66–1.82(2H, m), 2.68(2H, t), 3.12(3H, s), 3.99(3H, s), 5.03(2H, s), 5.33(2H, s), 7.05–7.14 (4H, m), 7.41(1H, dd), 7.50–7.76(6H, m) |

WORKING EXAMPLE 23

2-n-Butyl-3-[[2'-(1H-tetrazol-5-yl)biphenyl-4-yl]methyl]-4(3H)-quinazolinone

A solution of the compound (0.721 g, 1.50 mmol) obtained in Working Example 17 in trifluoroacetic acid (15 ml) was stirred at 50° C. for 5 hours. After cooling, the reaction mixture was concentrated in vacuo. The resulting residue was purified by flash column chromatography on silica gel. The column was eluted with chloroform-methanol (1% to 5%) to give 0.464 g (70.9%) of the title compound as a colorless crystal (recrystallization from ethyl acetate-isopropyl ether).

mp: 180.5°–181.5° C.
IR (KBr): 2965, 1668, 1592 cm$^{-1}$.

$^1$H-NMR (CDCl$_3$) δ: 0.92(3H, t, J=7.2 Hz, (CH$_2$)$_3$CH$_3$), 1.33–1.52 (2H, m, (CH$_2$)$_2$CH$_2$CH$_3$), 1.70–1.85(2H, m, CH$_2$CH$_2$CH$_2$CH$_3$), 2.75(2H, t, J=7.6 Hz, CH$_2$(CH$_2$)$_2$CH$_3$), 5.37(2H, s, CH$_2$Ar), 7.14(4H, s, ArH), 7.36–7.78, 8.02–8.07, 8.14–8.19(8H, m, ArH).

| Elemental Analysis for C$_{26}$H$_{24}$N$_6$O | | |
|---|---|---|
| C (%) | H (%) | N (%) |
| Calcd: C, 71.54; | H, 5.54; | N, 19.25 |
| Found: C, 71.51; | H, 5.47; | N, 19.25 |

The following compounds as listed in Tables 5a and 5b were prepared from the compounds obtained in Working Examples 18–21 in the same manner as in Working Example 23.

TABLE 5a

[Structural diagram of a biphenyl-tetrazole quinazolinone compound with numbered positions 1-8, featuring N=N/N-NH tetrazole ring, biphenyl, CH₂-N, C=O, and N with butyl chain; R substituent on the right benzene ring]

| Working Example No. | R | Appearance mp (°C.) | IR(KBr, cm⁻¹) | E. Anal. (Calcd/Found) C (%), H (%), O (%) |
|---|---|---|---|---|
| 24 | 7-NO₂ | colorless crystal 191–192 | 2970, 1690, 1590, 1532, 1340 | C₂₆H₂₃N₇O₃ C, 64.86; H, 4.81; N, 20.36 C, 65.07; H, 4.81; N, 20.16 |
| 25 | 7-Cl | colorless crystal 206.5–207.5 | 2960, 1668, 1592, 1560 | C₂₆H₂₃N₆OCl C, 66.31; H, 4.92; N, 17.84 C, 66.30; H, 4.86; N, 18.05 |
| 26 | 5-CH₃ | colorless crystal 201–202 | 2960, 1679, 1599, 1570 | C₂₇H₂₆N₆O C, 71.98; H, 5.82; N, 18.65 C, 71.99; H, 5.82; N, 18.76 |
| 27 | 6-Cl | colorless crystal 203–204 | 2960, 1675, 1595, 1565 | C₂₆H₂₃N₆OCl C, 66.31; H, 4.92; N, 17.84 C, 66.44; H, 4.78; N, 17.77 |

TABLE 5b

| Working Example No. | ¹H-NMR (CDCl₃) δ |
|---|---|
| 24 | 0.96(3H, t, J=7.2Hz, (CH₂)₃$\underline{CH_3}$), 1.36–1.55(2H, m, (CH₂)₂$\underline{CH_2}$CH₃), 1.76–1.91(2H, m, CH₂$\underline{CH_2}$CH₂CH₃), 2.83(2H, t, J=7.4Hz, $\underline{CH_2}$(CH₂)₂CH₃), 5.42(2H, s, $\underline{CH_2}$Ar), 7.21(4H, s, ArH), 7.38–7.42, 7.50–7.65, 8.08–8.12(4H, m, ArH), 8.21(1H, d-d, J=2.2Hz, 8.8Hz, ArH), 8.40(1H, d, J=8.8Hz, ArH), 8.53(1H, d, J=2.2Hz, ArH) |
| 25 | 0.93(3H, t, J=7.2Hz, (CH₂)₃$\underline{CH_3}$), 1.33–1.52(2H, m, (CH₂)₂$\underline{CH_2}$CH₃), 1.70–1.85(2H, m, CH₂$\underline{CH_2}$CH₂CH₃), 2.75(2H, t, J=7.4Hz, $\underline{CH_2}$(CH₂)₂CH₃), 5.36(2H, s, $\underline{CH_2}$Ar), 7.16(4H, s, ArH), 7.36–7.41, 7.49–7.66, 8.05–8.13(7H, m, ArH) |
| 26 | 0.93(3H, t, J=7.2Hz, (CH₂)₃$\underline{CH_3}$), 1.33–1.52(2H, m, (CH₂)₂$\underline{CH_2}$CH₃), 1.70–1.85(2H, m, CH₂$\underline{CH_2}$CH₂CH₃), 2.71(2H, t, J=7.4Hz, $\underline{CH_2}$(CH₂)₂CH₃), 2.78(3H, s, Ar$\underline{CH_3}$), 5.31(2H, s, $\underline{CH_2}$Ar), 7.10–7.21(5H, m, ArH), 7.36–7.62, 8.03–8.08(6H, m, ArH) |
| 27 | 0.94(3H, t, J=7.2Hz, (CH₂)₃$\underline{CH_3}$), 1.34–1.53(2H, m, (CH₂)₂$\underline{CH_2}$CH₃), 1.72–1.87(2H, m, CH₂$\underline{CH_2}$CH₂CH₃), 2.77(2H, t, J=7.6Hz, $\underline{CH_2}$(CH₂)₂CH₃), 5.38(2H, s, $\underline{CH_2}$Ar), 7.17(4H, s, ArH), 7.37–7.42, 7.53–7.64(4H, m, ArH), 7.68(1H, d-d, J=2.2Hz, 8.6Hz, ArH), 8.06–8.11(1H, m, ArH), 8.17(1H, d, J=2.2Hz, ArH) |

WORKING EXAMPLE 28

2-n-Butyl-6-hydroxy-3-[[2'-(1H-tetrazol-5-yl)biphenyl-4-yl]-methyl]-4(3H)-quinazolinone A solution of the compound (1.16 g, 2.0 mmol) obtained in Working Example 22 in trifluoroacetic acid (20 ml) was stirred at 50° C. for 3.5 hours. The reaction mixture was concentrated in vacuo, and the resulting residue was dissolved in dichloromethane. The solution was washed, dried (MgSO₄) and evaporated in vacuo. To a solution of the resulting pale yellow powder in methanol (10 ml) was added 1N aqueous sodium hydroxide (5 ml) and the solution was stirred at room temperature for 45 minutes. After addition of 1N hydrochloric acid (6 ml), the reaction mixture was extracted with ethyl acetate. The organic layer was washed with saturated aqueous sodium chloride, dried (MgSO₄) and evaporated in vacuo. The resulting residue was purified by flash column chromatography on silica gel. The column was eluted with chloroform-methanol (1% to 5%) to give the title compound.

¹H-NMR (CDCl₃) δ: 0.91(3H, t, J=7.2 Hz, (CH₂)₃$\underline{CH_3}$), 1.31–1.48 (2H, m, (CH₂)₂$\underline{CH_2}$CH₃), 1.67–1.82(2H, m, CH₂$\underline{CH_2}$CH₂CH₃), 2.71(2H, t, J=7.6 Hz, $\underline{CH_2}$(CH₂)₂CH₃), 5.34(2H, s, $\underline{CH_2}$Ar), 7.04–7.14(4H, m, ArH), 7.28–7.59(5H, m, ArH), 7.63(1H, d, J=2.8 Hz, ArH), 7.80(1H, d-d, J=1.8 Hz, 7.2 Hz, ArH)

REFERENCE EXAMPLE 16

2-n-Butyl-6-hydroxy-3-[[2'-(N-methoxymethyltetrazol-5-yl)biphenyl-4-yl]methyl]-4(3H)-quinazolinone A solution of 2-n-Butyl-3-[[2'-(N-methoxymethyltetrazol-5-yl)biphenyl-4-yl]methyl]-6-valeryloxy-4(3H)-quinazolinone (4.03 g) in a mixture of methanol (20 ml), THF (10 ml) and 1N aqueous sodium hydroxide (20 ml) was stirred at room temperature for 1 hour. After addition of 1N hydrochloric acid (25 ml), the reaction mixture was extracted with ethyl acetate. The organic layer was washed with water, dried and concentrated to dryness. The resulting crystalline product was recrystallized from ethyl acetate-hexane to give colorless crystals (3.13 g, 91%), mp. 157°–159° C.

$^1$H-NMR (200 MHz, CDCl$_3$) δ: 0.92(3H, t), 1.33–1.51(2H, m), 1.64–1.84(2H, m), 2.75(2H, t), 3.26(3H, s), 5.40(2H, s), 5.69(2H, s), 7.09(2H, d), 7.16(2H, d), 7.26–7.62(6H, m), 7.84–7.89(2H, m).

The following compounds in Tables 6a and 6b were prepared according to the procedure for Working Example 17.

TABLE 6a

| Reference Example No. | R$^1$ | R | mp (°C.) | $^1$H-NMR (200 MHz, CDCl$_3$)δ |
|---|---|---|---|---|
| 17 | Bu | 5-F | oil | 0.94(3H, t), 1.33–1.52(2H, m), 1.69–1.85(2H, m), 2.75(2H, t), 3.28(3H, s), 5.36(2H, s), 5.71(2H, s), 7.09–7.20 (4H, m), 7.40–7.72(6H, m), 7.86–7.90 (1H, m) |
| 18 | Bu | 5-Cl | powder | 0.93(3H, t), 1.33–1.51(2H, m), 1.69–1.84(2H, m), 2.75(2H, t), 3.28(3H, s), 5.35(2H, s), 7.11(2H, d), 7.17(2H, d), 7.40–7.59(6H, m), 7.86–7.90(1H, m) |
| 19 | Bu | 5-CH$_2$OAc | powder | 0.93(3H, t), 1.33–1.52(2H, m), 1.69–1.84(2H, m), 2.18(3H, s), 2.74(2H, t), 3.28(3H, s), 5.36(2H, s), 5.71(2H, s), 5.84(2H, s), 7.09(2H, d), 7.16(2H, d), 7.40–7.75(6H, m), 7.85–7.90(1H, m) |
| 20 | Bu | 6-OMe 7-OMe | 150–152 | 0.92(3H, t), 1.32–1.50(2H, m), 1.67–1.82(2H, m), 2.70(2H, t), 3.13(3H, s), 4.00(3H, s), 4.01(3H, s), 5.04(3H, s), 5.37(2H, s), 7.11(5H, s), 7.47–7.70 (5H, m) |
| 21 | Bu | 6-OMe 7-OMe 8-OMe | 134–135 | 0.92(3H, t), 1.32–1.49(2H, m), 1.73–1.87(2H, m), 2.72(2H, t), 3.12(3H, s), 3.97(3H, s), 4.04(3H, s), 4.12(3H, s), 5.03(2H, s), 5.37(2H, s), 7.11(4H, s), 7.47–7.71(5H, m) |
| 22 | Bu | 8-OCOBu | powder | 0.90(3H, t), 0.99(3H, t), 1.28–1.61 (4H, m), 1.67–1.89(4H, m), 2.66(2H, t), 2.70(2H, t), 3.13(3H, s), 5.03(2H, s), 5.33(2H, s), 7.11(4H, s), 7.39–7.77 (6H, m), 8.15–8.20(1H, m) |
| 23 | Pr | 6-OH | 188–190 | 1.01(3H, t), 1.73–1.91(2H, m), 2.73 (2H, t), 3.26(3H, s), 5.40(2H, s), 5.69(2H, s), 6.99(1H, brs), 7.09(2H, d), 7.16(2H, d), 7.31(1H, dd), 7.39–7.55 (3H, m), 7.60(1H, d), 7.82–7.89(2H, m) |
| 24 | Pr | 6-OCOPr | solid | 1.01(3H, t), 1.07(3H, t), 1.72–1.90 (4H, m), 2.59(2H, t), 2.73(2H, t), 3.28 (3H, s), 5.40(2H, s), 5.71(2H, s), 7.09 (2H, d), 7.17(2H, d), 7.40–7.59(4H, m), 7.69(1H, d), 7.86–7.90(1H, m), 7.97 (1H, d) |

REFERENCE EXAMPLE 25

2-Butyl-6-methoxy-3-[[2'-(N-methoxymethyltetrazol-5-yl)biphenyl-4-yl]methyl]-4(3H)-quinazolinone To a solution of sodium (28 mg) in methanol (3 ml) was added a solution of 2-butyl-6-hydroxy-3-[[2'-(N-methoxymethyltetrazol-5-yl)biphenyl-4-yl]methyl]-4(3H)-quinazolinone (0.6 g) in methanol (5 ml) and THF (5 ml) at 0° C. The solution was stirred at room temperature for 1 hour and evaporated to dryness. The residue was dissolved in DMF (5 ml) and methyl iodide (0.15 ml) was added to the solution. The mixture was stirred at room temperature for 17 hours, poured into water and extracted with ethyl acetate. The extract was washed with water, dried and evaporated to dryness. The residue was purified by column chromatography on silica gel to give a crystalline product. Recrystallization from ether-hexane gave colorless crystals (0.48 g, 78%).

mp: 130°–1310° C.

| Elemental Analysis for $C_{29}H_{30}N_6O_3$ | | | |
| --- | --- | --- | --- |
| | C (%) | H (%) | N (%) |
| Calcd: | C, 68.22; | H, 5.92; | N, 16.46 |
| Found: | C, 68.10; | H, 5.92; | N, 16.45 |

$^1$H-NMR (200 MHz, CDCl$_3$) δ: 0.93(3H, t), 1.34–1.52(2H, m), 1.69–1.84(2H, m), 2.74(2H, t), 3.27(3H, s), 3.92(3H, s), 5.41 (2H, s), 5.71(2H, s), 7.10(2H, d), 7.16(2H, d), 7.32–7.66 (6H, m), 7.85–7.89(1H, m)

REFERENCE EXAMPLE 26

2-Butyl-6-methoxycarbonylmethyl-3-[[2'-(N-methoxymethyltetrazol-5-yl)biphenyl-4-yl]methyl]-4(3H)-quinazolinone The title compound was obtained as a white powder in 93% yield from 6-hydroxy derivative according to the procedure for Reference Example 25.

$^1$H-NMR (200 MHz, CDCl$_3$) δ: 0.93(3H, t), 1.33–1.51(2H, m), 1.68–1.83(2H, m), 2.74(2H, t), 3.28(3H, s), 3.83(3H, s), 4.76(2H, s), 5.40(2H, s), 5.71(2H, s), 7.10(2H, d), 7.17 (2H, d), 7.40–7.66(6H, m), 7.85–7.90(2H, m).

REFERENCE EXAMPLE 27

2-Butyl-5-methoxymethyl-3-[[2'-(N-methoxymethyltetrazol-5-yl)biphenyl-4-yl]methyl]-4(3H)-quinazolinone The title compound was prepared according to the procedure for Reference Example 25 from 5-hydroxymethyl derivative.

Pale yellow oil.

$^1$H-NMR (200 MHz, CDCl$_3$) δ: 0.94(3H, t), 1.33–1.52(2H, m), 1.69–1.85(2H, m), 2.75(2H, t), 3.28(3H, s), 3.56(3H, s), 5.18(2H, s), 5.36(2H, s), 5.71(2H, s), 7.08(2H, d), 7.17 (2H, d), 7.40–7.89(7H, m).

REFERENCE EXAMPLE 28

2-Butyl-6-(2-chloroethyloxy)-3-[[2'-(N-methoxymethyltetrazol-5-yl)biphenyl-4-yl]methyl]-4(3H)-quinazolinone The title compound was obtained as a colorless syrup in 58% yield from 2-butyl-6-hydroxy-3-[[2'-(N-methoxymethyltetrazol-5-yl)biphenyl-4-yl]methyl]-4(3H)-quinazolinone according to the procedure for Reference Example 25.

$^1$H-NMR (200 MHz, CDCl$_3$) δ: 0.93(3H, t), 1.33–1.52(2H, m), 1.69–1.84(2H, m), 2.74(2H, t), 3.28(3H, s), 3.87(2H, t), 4.36(2H, t), 5.41(2H, s), 5.71(2H, s), 7.10(2H, d), 7.17 (2H, d), 7.36–7.66(6H, m), 7.85–7.90(1H, m).

REFERENCE EXAMPLE 29

6-(2-Acetoxyethyloxy)-2-butyl-3-[[2'-(N-methoxymethyltetrazol-5-yl)biphenyl-4-yl]methyl]-4(3H)-quinazolinone A mixture of 2-butyl-6-(2-chloroethyloxy)-3-[[2'-(N-methoxymethyltetrazol-5-yl)biphenyl-4-yl]methyl]-4(3H)-quinazolinone (0.59 g), sodium iodide (0.16 g) and sodium acetate (0.87 g) in DMF (15 ml) was stirred at 80° C. for 3 days. The reaction mixture was concentrated to dryness and the residue was extracted with ethyl acetate. The extract was washed with water, dried and concentrated to dryness. The residue was purified by column chromatography on silica gel to give a colorless oil (0.42 g, 68%).

$^1$H-NMR (200 MHz, CDCl$_3$) δ: 0.93(3H, t), 1.33–1.52(2H, m), 1.69–1.84(2H, m), 2.12(3H, s), 2.74(2H, t), 3.28(3H, s), 4.29 (2H, dd), 4.48(2H, dd), 5.41(2H, s), 5.71(2H, s), 7.10(2H, d), 7.17(2H, d), 7.35–7.66(6H, m), 7.85–7.90(1H, m)

REFERENCE EXAMPLE 30

6-(2-Hydroxyethyloxy)-3-[[2'-(N-methoxymethyltetrazol-5-yl)biphenyl-4-yl]methyl]-2-propyl-4(3H)-quinazolinone A solution of 6-(2-acetoxyethyloxy)-3-[[2'-(N-methoxymethyltetrazol-5-yl)biphenyl-4-yl]methyl]-2-propyl-4(3H)-quinazolinone (0.42 g) in a mixture of methanol (3 ml), THF (2 ml) and 1N aqueous sodium hydroxide (1.5 ml) was stirred at room temperature for 1 hour. After addition of 1N hydrochloric acid (1.5 ml), the reaction mixture was extracted with ethyl acetate and the extract was washed with water, dried and evaporated to dryness. The residue was purified by column chromatography on silica gel to give a white powder.

$^1$H-NMR (200 MHz, CDCl$_3$) δ: 1.01(3H, t), 1.73–1.92(2H, m), 2.07 (1H, brs), 2.72(2H, t), 3.27(3H, s), 4.01–4.03(2H, m), 4.21(2H, dd), 5.40(2H, s), 5.70(2H, s), 7.09(2H, d), 7.16 (2H, d), 7.34–7.67(6H, m), 7.84–7.89(1H, m)

REFERENCE EXAMPLE 31

2-Butyl-6-(2-hydroxyethyloxy)-3-[[2'-(N-methoxymethyltetrazol-5-yl)biphenyl-4-yl]methyl]-4(3H)-quinazolinone The title compound was prepared from acetoxyethyloxy derivative according to the procedure for Reference Example 30.

REFERENCE EXAMPLE 32

2-Butyl-6-carboxymethyloxy-3-[[2'-(N-methoxymethyltetrazol-5-yl)biphenyl-4-yl]methyl]-4(3H)-quinazolinone The title compound was prepared from methoxycarbonylmethyloxy derivative according to the procedure for Reference Example 40.

REFERENCE EXAMPLE 33

6-(2-Benzoyloxyethyloxy)-3-[[2'-(N-methoxymethyltetrazol-5-yl)-biphenyl-4-yl]methyl]-2-propyl-4(3H)-quinazolinone To a solution of 6-(2-hydroxyethyloxy)-3-[[2'-(N-methoxymethyltetrazol-5-yl)biphenyl-4-yl]methyl]-2-propyl-4(3H)-quinazolinone (0.09 g) in pyridine (2 ml) was added benzoyl chloride (0.08 ml) and the reaction solution was stirred at room temperature for 4 hours. The mixture was extracted with ethyl acetate-water and the organic layer was washed with water, dried and evaporated to dryness. The residue was purified by column chromatography on silica gel to give a colorless oil (0.1 g, 93%).

$^1$H-NMR (200 MHz, CDCl$_3$) δ: 1.01(3H, t), 1.73–1.91(2H, m), 2.72 (2H, t), 3.27(3H, s), 4.44(2H, dd), 4.72(2H, dd), 5.41 (2H, s), 5.70(2H, s), 7.09(2H,d), 7.16(2H, d), 7.36–7.72 (9H, m), 7.85–7.89(1H, m), 8.05–8.09(2H, m)

REFERENCE EXAMPLE 34

3-[[2'-(N-Methoxymethyltetrazol-5-yl)biphenyl-4-yl]methyl]-6-(2-nicotinoyloxyethyloxy)-2-propyl-4(3H)-quinazolinone The title compound was obtained as a colorless oil in 58% yield from hydroxyethyloxy derivative according to the procedure for Reference Example 33.

$^1$H-NMR (200 MHz, CDCl$_3$) δ: 1.01(3H, t), 1.73–1.91(2H, m), 2.73 (2H, t), 3.27(3H, s), 4.45(2H, t), 4.76(2H, t), 5.41 (2H, s), 5.71(2H, s), 7.10(2H, d), 7.17(2H, d), 7.35–7.59 (5H, m), 7.62(1H, d), 7.70(1H, d), 7.85–7.89(1H, m), 8.33 (1H, dt), 8.77(1H, dd), 9.25(1H, m).

REFERENCE EXAMPLE 35

6-[2-(4-Dimethylaminobenzoyloxy)ethyloxy]-3-[[2'-(N-methoxymethyltetrazol-5-yl)biphenyl-4-yl]methyl]-2-propyl-4(3H)-quinazolinone The title compound was obtained as a pale yellow powder in 54% yield from hydroxyethyloxy derivative according to the procedure for Reference Example 33.

$^1$H-NMR (200 MHz, CDCl$_3$) δ: 1.01(3H, t), 1.72–1.90(2H, m), 2.73 (2H, t), 3.07(6H, s), 3.27(3H, s), 3.80–4.34(4H, m), 5.40 (2H, s), 5.71(2H, s), 6.94(1H, d), 7.09(2H, d), 7.16 (2H, d), 7.27–7.64(7H, m), 7.84–7.89(1H, m), 8.09(1H, dd), 8.72(1H, dd).

REFERENCE EXAMPLE 36

6-Benzoyloxy-3-[[2'-(N-methoxymethyltetrazol-5-yl)biphenyl-4-yl]-methyl]-2-propyl-4(3H)-quinazolinone The title compound was obtained as a white powder in 82% yield from 6-hydroxy derivative according to the procedure for Reference Example 33.

$^1$H-NMR (200 MHz, CDCl$_3$) δ: 1.03(3H, t), 1.75–1.94(2H, m), 2.76 (2H, t), 3.28(3H, s), 5.41(2H, s), 5.71(2H, s), 7.10 (2H, d), 7.17(2H, d), 7.40–7.90(9H, m), 8.11(1H, d), 8.20–8.25(2H, m).

REFERENCE EXAMPLE 37

3-[[2'-(N-Methoxymethyltetrazol-5-yl)biphenyl-4-yl]methyl]-6-nicotinoyloxy-2-propyl-4(3H)-quinazolinone The title compound was obtained as a white powder in 78% yield from 6-hydroxy derivative according to the procedure for Reference Example 33.

$^1$H-NMR (200 MHz, CDCl$_3$) δ: 1.03(3H, t), 1.75–1.94(2H, m), 2.76 (2H, t), 3.29(3H, s), 5.42(2H, s), 5.71(2H, s), 7.11 (2H, d), 7.18(2H, d), 7.41–7.90(7H, m), 8.14(1H, d), 8.48(1H, dt), 8.89(1H, dd), 9.42–9.44(1H, m).

REFERENCE EXAMPLE 38

3-[[2'-(N-Methoxymethyltetrazol-5-yl)biphenyl-4-yl]methyl]-6-(N-propylcarbamoyloxy)-2-propyl-4(3H)-quinazolinone A mixture of 6-hydroxy-3-[[2'-(N-methoxymethyltetrazol-5-yl)biphenyl-4-yl]methyl]-2-propyl-4(3H)-quinazolinone (0.15 g) propyl isocyanate (0.9 ml) in a mixture of THF (5 ml) and pyridine (2 ml) was heated under reflux for 6 days. The reaction mixture was diluted with ethyl acetate and the solution was washed with 1N hydrochloric acid and water, dried and concentrated to dryness. The residue was purified by column chromatography on silica gel to give a pale yellow powder (0.14 g, 79%).

$^1$H-NMR (200 MHz, CDCl$_3$) δ: 0.96(3H, t), 1.00(3H, t), 1.51–1.68 (2H, m), 1.72–1.91(2H, m), 2.78(2H, t), 3.18–3.28(2H, m), 3.27(3H, s), 5.39(2H, s), 5.52(1H, t), 5.70(2H, s), 7.08(2H, d), 7.16(2H, d), 7.39–7.70(5H, m), 7.84–7.89 (1H, m), 7.99(1H, d).

REFERENCE EXAMPLE 39

3-[[2'-(N-Methoxymethyltetrazol-5-yl)biphenyl-4-yl]methyl]-6-(N-phenylcarbamoyloxy)-2-propyl-4(3H)-quinazolinone The title compound was obtained as a white powder in 92% yield from 6-hydroxy derivative according to the procedure for Reference Example 38.

$^1$H-NMR (200 MHz, CDCl$_3$) δ: 1.00(3H, t), 1.74–1.93(2H, m), 2.74 (2H, t), 3.27(3H, s), 5.41(2H, s), 5.69(2H, s), 7.07–7.18 (1H, m), 7.09(2H, d), 7.17(2H, d), 7.29–7.73(10H, m), 7.85–7.89(1H, m), 8.10(1H, d).

REFERENCE EXAMPLE 40

3-[[2'-(N-Methoxymethyltetrazol-5-yl)biphenyl-4-yl]methyl]-6-[(1-morpholinocarbamoyl)methyloxy]-2-propyl-4(3H)-quinazolinone To a mixture of 6-methoxycarbonylmethyloxy-3-[[2'-(N-methoxymethyltetrazol-5-yl)biphenyl-4-yl]methyl]-2-propyl-4(3H)-quinazolinone (0.4 g) in a mixture of methanol (4 ml) and THF (2 ml) was added 1N sodium hydroxide (4 ml) and the mixture was stirred at room temperature for 15 hours. After addition of 1N hydrochloric acid (5 ml), the resulting mixture was extracted with ethyl acetate and the extract was washed with water, dried and evaporated to dryness. To a stirred cold solution of the resulting syrup, morpholine (0.01 ml) and diethylphosphorocyanidate (0.26 g) in DMF (4 ml) was added dropwise triethylamine (0.2 ml) and the reaction mixture was stirred at 0° C. for 1 hour and then at room temperature for 15 hours. After evaporation of the solvent, the resulting syrup was dissolved in ethyl acetate and the solution was washed with water, dried and evaporated to dryness. The residue was purified by column chromatography on silica gel to give a white powder (0.42 g, 97%).

$^1$H-NMR (200 MHz, CDCl$_3$) δ: 1.01(3H, t), 1.72–1.91(2H, m), 2.72 (2H, t), 3.28(3H, s), 3.53–3.74(8H, m), 4.80(2H, s), 5.39(2H, s), 5.71(2H, s), 7.09(2H, d), 7.16(2H, d), 7.39–7.66(6H, m), 7.84–7.89(1H, m)

REFERENCE EXAMPLE 41

6-(N-Benzylcarbamoylmethyloxy)-3-[[2'-(N-methoxymethyltetrazol-5-yl)biphenyl-4-yl]methyl]-2-propyl-4(3H)-quinazolinone The title compound was obtained as a white powder in 94% yield according to the procedure for Reference Example 40.

$^1$H-NMR (200 MHz, CDCl$_3$) δ: 1.01(3H, t), 1.72–1.91(2H, m), 2.72 (2H, s), 3.27(3H, s), 4.57(2H, d), 4.66(2H, s), 5.40 (2H, s), 5.70(2H, s), 6.90(1H, t), 7.08(2H, d), 7.16 (2H, d), 7.27–7.65(10H, m), 7.69(1H, d), 7.84–7.89 (1H, m).

REFERENCE EXAMPLE 42

6-Methoxycarbamoylmethoxy-3-[[2'-(N-methoxymethyltetrazol-5-yl)-biphenyl-4-yl]methyl]-2-propyl-4(3H)-quinazolinone The title compound was obtained as a white powder in 86% yield from 6-hydroxyl derivative according to the procedure for Reference Example 40.

$^1$H-NMR (200 MHz, CDCl$_3$) δ: 1.00(3H, t), 1.72–1.91(2H, m), 2.72 (2H, t), 3.27(3H, s), 3.82(3H, s), 4.76(2H, s), 5.40 (2H, s), 5.70(2H, s), 7.09(2H, d), 7.17(2H, d), 7.39–7.66 (6H, m), 7.84–7.89(1H, m).

REFERENCE EXAMPLE 43

2-Propyl-3-[[2'-(N-trityltetrazol-5-yl)biphenyl-4-yl]methyl]-4(3H)-quinazolinone To a stirred mixture of sodium hydride (60% dispersion in mineral oil, 0.3 g) in DMF (50 ml) was added 2-propyl-4(3H)-quinazolinone (1.0 g) and the mixture was stirred at room temperature for 15 minutes. After addition of 4-[2'-(N-trityltetrazol-5-yl)phenyl]benzyl bromide (5.0 g), the reaction mixture was stirred at room temperature for 19 hours and concentrated to dryness. The residue was extracted with ethyl acetate-water and the organic layer was washed with water, dried and concentrated to dryness. The resulting syrup was purified by column chromatography on silica gel to give a colorless amorphous (2.34 g, 66%).

$^1$H-NMR (200 MHz, CDCl$_3$) δ: 0.94(3H, t), 1.77(2H, m), 2.64(2H, t), 5.31(2H, s), 6.8–7.6(23H, m), 7.6–8.0(3H, m), 8.32 (1H, dd).

The following compounds were prepared according to the procedure for Reference Example 43.

REFERENCE EXAMPLE 44

2-Methyl-3-[[2'-(N-trityltetrazol-5-yl)biphenyl-4-yl]methyl]-4(3H)-quinazolinone Colorless powder (60% yield).

$^1$H-NMR (200 MHz, CDCl$_3$) δ: 2.41(3H, s), 5.28(2H, s), 6.8–7.6 (23H, m), 7.6–8.0(3H, m), 8.38(1H, dd).

REFERENCE EXAMPLE 45

2-Ethyl-3-[[2'-(N-trityltetrazol-5-yl)biphenyl-4-yl]methyl]-4(3H)-quinazolinone

Colorless powder (20% yield).

$^1$H-NMR (200 MHz, CDCl$_3$) δ: 1.25(3H, t), 2.09(3H, s), 2.61(2H, q), 5.15(2H, s), 6.8–7.8(30H, m).

REFERENCE EXAMPLE 46

2-Methylthio-3-[[2'-(N-trityltetrazol-5-yl)biphenyl-4-yl]methyl]-4(3H)-quinazolinone Yellow powder (54% yield).

$^1$H-NMR (200 MHz, CDCl$_3$) δ: 2.53(3H, s), 5.28(2H, s), 6.8–7.6 (23H, m), 7.55–8.0(3H, m), 8.26(1H, dd).

REFERENCE EXAMPLE 47

2-Ethylthio-3-[[2'-(N-trityltetrazol-5-yl)biphenyl-4-yl]methyl]-4(3H)-quinazolinone Colorless powder (39% yield).

$^1$H-NMR (200 MHz, CDCl$_3$) δ: 1.36(3H, t), 3.21(2H, q), 5.27(2H, s), 6.8–7.5(23H, m), 7.5–8.0(3H, m), 8.25(1H, dd).

REFERENCE EXAMPLE 48

2-Ethoxy-3-[[2'-(N-trityltetrazol-5-yl)biphenyl-4-yl]methyl]-4(3H)-quinazolinone A mixture of 2-ethylthio-3-[[2'-(N-trityltetrazol-5-yl)biphenyl-4-yl]methyl]-4(3H)-quinazolinone (0.5 g) and sodium ethoxide (182 mg) in ethanol (20 ml) was stirred at room temperature for 3 days. The reaction mixture was concentrated to dryness. The residue was extracted using methylene chloride and an aqueous solution of ammonium chloride. The organic layer was washed with water, dried and evaporated to dryness. The resulting syrup was purified by column chromatography on silica gel to give a colorless oil (72 mg, 21%).

$^1$H-NMR (200 MHz, CDCl$_3$) δ: 1.36(3H, t), 4.47(2H, q), 5.19(2H, s), 6.85–7.50(23H, m), 7.50–8.00(3H, m), 8.21(1H, dd).

REFERENCE EXAMPLE 49

1-[(2'-Cyanobiphenyl-4-yl)methyl]-2-ethylquinazolin-4(1H)-one

A mixture of 1-[(2'-cyanobiphenyl-4-yl)methyl]isatoic anhydride (0.15 g) and thiopropionamide (0.138 g) was stirred at 180° C. for 2 hours. After cooling, the mixture was purified by column chromatography on silica gel to give a crystalline product. Recrystallization from ethyl acetate-ether gave yellow crystals (87 mg, 56%).

mp: 207°–208° C.

$^1$H-NMR (200 MHz, CDCl$_3$) δ: 1.41(3H, t), 2.86(2H, q), 5.51(2H, s), 7.22–7.30(3H, m), 7.38–7.79(8H, m), 8.36(1H, dd).

REFERENCE EXAMPLE 50

2-Butyl-1-[(2'-cyanobiphenyl-4-yl)methyl]quinazolin-4(1H)-one

The title compound was obtained according to the procedure for Reference Example 49 as yellow crystals (52% yield).

mp: 141°–143° C.

$^1$H-NMR (200 MHz, CDCl$_3$) δ: 0.94(3H, t), 1.36–1.55(2H, m), 1.82–1.97(2H, m), 2.84(2H, t), 5.48(2H, s), 7.23–7.26 (3H, m), 7.41–7.51(3H, m), 7.55–7.81(5H, m), 8.41 (1H, dd).

REFERENCE EXAMPLE 51

2-Butyl-5-methoxycarbonyl-3-[[2'-(N-methoxymethyltetrazol-5-yl)biphenyl-4-yl]methyl]-4(3H)-quinazolinone The title compound was prepared according to the procedure for Working Example 17, as a pale yellow solid (21% yield).

$^1$H-NMR (200 MHz, CDCl$_3$) δ: 0.92(3H, t), 1.30–1.48(2H, m), 1.66–1.82(2H, m), 2.68(2H, t), 3.12(3H, s), 3.99(3H, s), 5.03(2H, s), 5.33(2H, s), 7.05–7.14(4H, m), 7.41(1H, dd), 7.50–7.76(6H, m).

The following compounds in Tables 7a and 7b were prepared according to the procedure for Working Example 23.

TABLE 7a

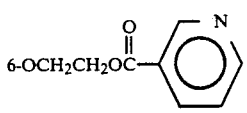

| Working Example No. | $R^1$ | R | mp (°C.) Yield (%) | E. Anal. (Calcd/Found) C (%), H (%), O (%) |
|---|---|---|---|---|
| 29 | Bu | 6-OCOBu | 137–140 31 | $C_{31}H_{32}N_6O_3$<br>C, 69.38; H, 6.01; N, 15.66<br>C, 69.29; H, 5.99; N, 15.62 |
| 30 | Bu | 5-F | 210–211 59 | $C_{26}H_{23}FN_6O \cdot 0.2AcOEt$<br>C, 68.18; H, 5.25; N, 17.80<br>C, 68.18; H, 5.23; N, 17.89 |
| 31 | Bu | 5-Cl | 228–229 65 | $C_{26}H_{23}ClN_6O \cdot 0.2AcOEt$<br>C, 65.88; H, 5.07; N, 17.20<br>C, 65.71; H, 5.10; N, 17.08 |
| 32 | Bu | 5-CH$_2$OAc | 205–206 52 | $C_{29}H_{28}N_6O_3$<br>C, 68.49; H, 5.55; N, 16.52<br>C, 68.46; H, 5.49; N, 16.52 |
| 33 | Bu | 6-OMe<br>7-OMe | 137–139 81 | $C_{28}H_{28}N_6O_3 \cdot H_2O$<br>C, 65.36; H, 5.88; N, 16.33<br>C, 65.45; H, 5.81; N, 16.41 |
| 34 | Bu | 6-OMe<br>7-OMe<br>8-OMe | 123–124 80 | $C_{29}H_{30}N_6O_9 \cdot 0.4H_2O$<br>C, 65.25; H, 5.82; N, 15.74<br>C, 65.47; H, 5.74; N, 15.80 |
| 35 | Bu | 6-OH | 168–169 34 | $C_{31}H_{32}N_6O_3$<br>C, 69.38; H, 6.01; N, 15.66<br>C, 69.30; H, 6.32; N, 15.62 |
| 36 | Pr | 6-OH | 231–233 65 | $C_{25}H_{22}N_6O_2 \cdot 0.1H_2O$<br>C, 68.20; H, 5.08; N, 19.09<br>C, 68.31; H, 4.97; N, 18.84 |
| 37 | Bu | 6-OMe | 176–178 60 | $C_{27}H_{26}N_6O_2$<br>C, 69.51; H, 5.62; N, 18.01<br>C, 69.77; H, 5.71; N, 17.99 |
| 38 | Bu | 6-OCH$_2$COOMe | 92–95 87 | $C_{29}H_{28}N_6O_4 \cdot 0.2H_2O$<br>C, 65.95; H, 5.42; N, 15.91<br>C, 65.98; H, 5.38; N, 15.79 |
| 39 | Bu | 6-O(CH$_2$)$_2$OAc | 164–165 77 | $C_{30}H_{30}N_6O_4 \cdot 0.2H_2O$<br>C, 66.46; H, 5.65; N, 15.50<br>C, 66.47; H, 5.46; N, 15.38 |
| 40 | Pr | 6-O(CH$_2$)$_2$OAc | 178–180 83 | $C_{29}H_{28}N_6O_4 \cdot 0.2AcOEt$<br>C, 66.01; H, 5.50; N, 15.50<br>C, 65.80; H, 5.53; N, 15.31 |
| 41 | Pr | 6-OCH$_2$CH$_2$OBzo | 117–118 65 | $C_{34}H_{30}N_6O_4 \cdot 0.4AcOEt$<br>C, 68.78; H, 5.38; N, 13.51<br>C, 68.78; H, 5.45; N, 13.33 |
| 42 | Pr | 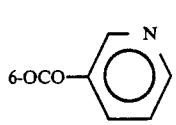 | 109–110 70 | $C_{33}H_{29}N_7O_4 \cdot 0.3AcOEt$<br>C, 66.89; H, 5.15; N, 15.97<br>C, 66.93; H, 4.87; N, 15.68 |
| 43 | Pr | 6-OCOPh | 165–167 88 | $C_{32}H_{26}N_6O_3 \cdot 2.3H_2O$<br>C, 65.81; H, 5.28; N, 14.39<br>C, 65.92; H, 5.14; N, 14.26 |
| 44 | Pr | 6-OCO—⟨pyridyl⟩ | 232–233 43 | $C_{31}H_{25}N_7O_3 \cdot 0.4H_2O$<br>C, 67.60; H, 4.72; N, 17.80<br>C, 67.86; H, 4.86; N, 17.61 |
| 45 | Pr | 6-OCONHPr | 207–208 53 | $C_{29}H_{29}N_7O_3 \cdot 0.2H_2O$<br>C, 66.07; H, 5.62; N, 18.60<br>C, 66.04; H, 5.56; N, 18.40 |
| 46 | Pr | 6-OCONHPh | 180–182 69 | $C_{32}H_{27}H_7O_3$<br>C, 68.93; H, 4.88; N, 17.58<br>C, 68.66; H, 4.67; N, 17.54 |
| 47 | Pr | 6-OCH$_2$COOMe | 181–182 80 | $C_{28}H_{26}N_6O_4$<br>C, 65.87; H, 5.13; N, 16.46<br>C, 65.63; H, 5.14; N, 16.30 |

TABLE 7a-continued

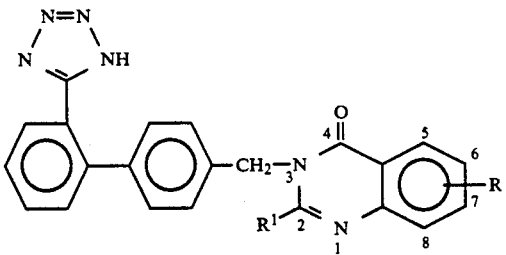

| Working Example No. | R¹ | R | mp (°C.) Yield (%) | E. Anal. (Calcd/Found) C (%), H (%), O (%) |
|---|---|---|---|---|
| 48 | Pr | 6-OCH₂CON◯O | 123-126 69 | $C_{31}H_{31}N_7O_4 \cdot 0.3H_2O$ C, 65.20; H, 5.58; N, 17.17 C, 65.20; H, 5.30; N, 17.08 |
| 49 | Pr | 6-OCH₂CONHCH₂Ph | 125-129 53 | $C_{34}H_{31}N_7O_3 \cdot H_2O$ C, 67.65; H, 5.51; N, 16.24 C, 67.57; H, 5.26; N, 16.17 |
| 50 | Pr | 6-CH₂OMe | 223-226 53 | $C_{28}H_{28}N_6O_2$ C, 69.98; H, 5.87; N, 17.49 C, 69.69; H, 5.94; N, 17.21 |

TABLE 7b

| Working Example No. | ¹H-NMR (200 MHz, CDCl₃) δ |
|---|---|
| 29 | 0.93(3H,t),0.98(3H,t),1.33–1.56(4H,m),1.69–1.86(4H,m), 2.61(2H,t),2.77(2H,t),5.38(2H,s),7.16(4H,s),7.37–7.70 (5H,m),7.90(1H,d),8.05–8.09(1H,m) |
| 30 | (DMSO-d₆):0.84(3H,t),1.23–1.41(2H,m),1.58–1.73 (2H,m),2.71(2H,t),5.35(2H,s),7.08(2H,d),7.15(2H,d),7.22– 7.31(1H,m),7.44–7.86(6H,m) |
| 31 | (DMSO-d₆):0.84(3H,t),1.23–1.41(2H,m),1.58–1.74 (2H,m),2.71(2H,t),5.33(2H,s),7.08(2H,d),7.14(2H,d),7.51– 7.78(7H,m) |
| 32 | 0.93(3H,t),1.34–1.52(2H,m),1.71–1.86(2H,m),2.16(3H,s), 2.76(2H,t),5.32(2H,s),5.76(2H,s),7.15(4H,s),7.36–7.74 (6H,m),8.03–8.07(1H,m) |
| 33 | (DMSO-d₆):0.85(3H,t),1.23–1.41(2H,m),1.58–1.74 (2H,m),2.69(2H,t),3.88(3H,s),3.92(3H,s),5.38(2H,s),7.04– 7.13(5H,m),7.47–7.72(5H,m) |
| 34 | 0.93(3H,t),1.33–1.51(2H,m),1.75–1.90(2H,m),2.78(2H,t), 3.94(3H,s),4.01(3H,s),4.08(3H,s),5.39(2H,s),7.16(4H,s), 7.37–7.42(2H,m),7.48–7.63(2H,m),8.06–8.10(1H,m) |
| 35 | 0.92(3H,t),0.99(3H,t),1.31–1.60(4H,m),1.70–1.89(4H,m), 2.70(2H,t),2.74(2H,t),5.36(2H,s),7.11–7.20(4H,m),7.37–7.63 (5H,m),8.03–8.14(2H,m) |
| 36 | (DMSO-d₆):0.89(3H,t),1.59–1.77(2H,m),2.65(2H,t),5.36 (2H,s),7.03–7.14(4H,m),7.24–7.30(1H,m),7.43–7.73(6H,m), 10.06(1H,s) |
| 37 | 0.93(3H,t),1.33–1.51(2H,m),1.69–1.85(2H,m),2.75(2H,t), 3.89(3H,s),5.39(2H,s),7.15(4H,s),7.31–7.41(2H,m),7.49–7.63 (4H,m),8.05–8.10(1H,m) |
| 38 | 0.92(3H,t),1.33–1.51(2H,m),1.68–1.85(2H,m),2.75(2H,t), 3.81(3H,s),4.74(2H,s),5.37(2H,s),7.15(4H,s),7.36–7.62 (6H,m),8.04–8.09(1H,m) |
| 39 | 0.93(3H,t),1.33–1.52(2H,m),1.70–1.85(2H,m),2.11(3H,s), 2.75(2H,t),4.26(2H,dd),4.46(2H,dd),5.39(2H,s),7.16 (4H,s),7.34–7.41(2H,m),7.48–7.61(4H,m),8.06–8.10 (1H,m) |
| 40 | 1.03(3H,t),1.75–1.94(2H,m),2.76(2H,t),4.28(2H,dd),4.47 (2H,dd),5.41(2H,s),7.19(4H,s),7.36–7.43(2H,m),7.51–7.65 (4H,m),8.10–8.15(1H,m) |
| 41 | 1.02(3H,t),1.73–1.92(2H,m),2.74(2H,t),4.39–4.43(2H,m), 4.69–4.74(2H,m),5.39(2H,s),7.16(4H,s),7.36–7.66(9H,m), 8.04–8.10(3H,m) |
| 42 | 1.00(3H,t),1.72–1.90(2H,m),2.71(2H,t),4.45–4.49(2H,m), 4.74–4.78(2H,m),5.34(2H,s),7.07–7.16(4H,m),7.34–7.43 (3H,m),7.48–7.67(4H,m),8.02–8.07(1H,m),8.33(1H,dt), 8.66(1H,dd),9.15–9.16(1H,m) |
| 43 | (DMSO-d₆):1.14(3H,t),1.82–2.01(2H,m),3.31(2H,t),5,49 (2H,s),7.15(2H,d),7.21(2H,d),7.43–7.82(8H,m),8.19– 8.24(3H,m),8.50(1H,d) |
| 44 | (DMSO-d₆):0.92(3H,t),1.64–1.82(2H,m),2.73(2H,t),5.42 (2H,s),7.08(2H,d),7.15(2H,d),7.52–7.86(7H,m),8.09(1H,d), 8.52(1H,dt),8.92(1H,dd),9.31(1H,d) |
| 45 | (DMSO-d₆):0.90(3H,t),0.91(3H,t),1.42–1.60(2H,m),1.63– 1.80(2H,m),2.71(2H,t),3.06(2H,dt),5.39(2H,s),7.06(2H,d), 7.13(2H,d),7.50–7.71(6H,m),7.78(1H,d),7.91(1H,t) |
| 46 | (DMSO-d₆):0.92(3H,t),1.63–1.81(2H,m),2.72(2H,t),5.40 (2H,s),7.03–7.16(5H,m),7.30–7.38(2H,m),7.52–7.72(8H,m), 7.91–7.93(1H,m),10.36(1H,brs) |
| 47 | (DMSO-d₆):1.01(3H,t),1.72–1.91(2H,m),2.71(2H,t),3.83 (3H,s),4.76(2H,s),5.38(2H,s),7.07–7.17(4H,m),7.41–7.66 (6H,m),7.74–7.78(1H,m) |
| 48 | 1.00(3H,t),1.68–1.88(2H,m),2.71(2H,t),3.58–3.70(8H,m), 4.79(2H,s),5.31(2H,s),7.09(4H,s),7.35–7.59(6H,m), 7.94–7.98(1H,m) |
| 49 | 0.99(3H,t),1.68–1.87(2H,m),2.69(2H,t),4.54(2H,d),4.59 (2H,s),5.38(2H,s),6.96(1H,t),7.10(2H,d),7.16(2H,d),7.26– 7.38(7H,m),7.51–7.61(4H,m),7.99–8.04(1H,m) |
| 50 | (DMSO-d₆):0.84(3H,t),1.23–1.41(2H,m),1.58–1.73 (2H,m),2.70(2H,t),3.46(3H,s),5.06(2H,s),5.35(2H,s),7.07 (2H,d),7.13(2H,d),7.49–7.82(7H,m) |

WORKING EXAMPLE 51

2-Butyl-6-hydroxy-3-[[2'-(1H-tetrazol-5-yl)biphenyl-4-yl]methyl]-4(3H)-quinazolinone A mixture of 2-butyl-3-[[2'-(1H-tetrazol-5-yl)biphenyl-4-yl]methyl]-8-valeryloxy-4(3H)-quinazolinone (0.3 g) in methanol (5 ml) and 1N sodium hydroxide (2 ml) was stirred at room temperature for 1 hour. After addition of 1N hydrochloric acid, the reaction solution was extracted with ethyl acetate and the organic layer was washed with water, dried and evaporated to dryness. The residue was purified by column chromatography on silica gel to give a crystalline product. Recrystallization from ethyl acetate-ether gave colorless crystals (0.2 g, 80%), mp 212°–214° C.

| Elemental Analysis for $C_{26}H_{24}N_6O_2$ | | |
|---|---|---|
| C (%) | H (%) | N (%) |
| Calcd: C, 69.01; | H, 5.35; | N, 18.57 |
| Found: C, 68.85; | H, 5.28; | N, 18.47 |

$^1$H-NMR (200 MHz, DMSO-d$_6$) δ: 0.85(3H, t), 1.22–1.41(2H, m), 1.64–1.79(2H, m), 2.72(2H, t), 5.38(2H, s), 7.04–7.36 (6H, m), 7.49–7.71(5H, m), 9.42(1H, s).

WORKING EXAMPLE 52

2-Butyl-6-(carboxymethyloxy)-3-[[2'-(1H-tetrazol-5-yl)biphenyl-4-yl]methyl]-4(3H)-quinazolinone The title compound was obtained as colorless crystals in 72% yield from methoxycarbonylmethyl derivative according to the procedure for Working Example 51.
mp 205°–207° C.

| Elemental Analysis for $C_{28}H_{26}N_6O_4 \cdot 0.3H_2O$ | | |
|---|---|---|
| C (%) | H (%) | N (%) |
| Calcd: C, 65.18; | H, 5.20; | N, 16.29 |
| Found: C, 65.36; | H, 5.09; | N, 16.03 |

$^1$H-NMR (200 MHz, DMSO-d$_6$) δ: 0.84(3H, t), 1.23–1.41(2H, m), 1.58–1.73(2H, m), 2.70(2H, t), 4.83(2H, s), 5.38(2H, s), 7.06(2H, d), 7.11(2H, d), 7.41–7.71(7H, m)

WORKING EXAMPLE 53

6-(2-Hydroxyethyloxy)-2-propyl-3-[[2'-(1H-tetrazol-5-yl)biphenyl-4-yl]methyl]-4(3H)-quinazolinone The title compound was obtained as colorless crystals in 75% yield from acetoxyethyloxy derivative according to the procedure for Working Example 51.
mp 125°–127° C.

| Elemental Analysis for $C_{27}H_{26}N_6O_3 \cdot 0.25EtOAc$ | | |
|---|---|---|
| C (%) | H (%) | N (%) |
| Calcd: C, 66.65; | H, 5.59; | N, 16.66 |
| Found: C, 66.45; | H, 5.73; | N, 16.84 |

$^1$H-NMR (200 MHz, DMSO-d$_6$) δ: 1.01(3H, t), 1.73–1.92(2H, m), 2.71(2H, t), 4.00(2H, dd), 4.20(2H, dd), 5.39(2H, s), 7.07–7.17(4H, m), 7.36–7.65(6H, m), 7.76–7.80(1H, m)

WORKING EXAMPLE 54

2-Butyl-5-hydroxymethyl-3-[[2'-(1H-tetrazol-5-yl)biphenyl-4-yl]methyl]-4(3H)-quinazolinone The title compound was obtained according to the procedure for Working Example 51 as colorless crystals.
mp 230°–232° C.

| Elemental Analysis for $C_{27}H_{26}N_6O_2 \cdot 0.2H_2O$ | | |
|---|---|---|
| C (%) | H (%) | N (%) |
| Calcd: C, 68.98; | H, 5.56; | N, 17.88 |
| Found: C, 68.86; | H, 5.65; | N, 17.76 |

$^1$H-NMR (200 MHz, DMSO-d$_6$) δ: 0.84(3H, t), 1.22–1.41(2H, m), 1.58–1.73(2H, m), 2.69(2H, t), 5.10(2H, s), 5.27(1H, brs), 5.35(2H, s), 7.06(2H, d), 7.12(2H, d), 7.47–7.82(7H, m)

WORKING EXAMPLE 55

2-Butyl-6-(2-hydroxyethyloxy)-3-[[2'-(1H-tetrazol-5-yl)biphenyl-4-yl]-methyl]-4(3H)-quinazolinone The title compound was obtained as colorless crystals in 86% yield from acetoxyethyl derivative according to the procedure for Working Example 51.
mp 152°–154° C.

| Elemental Analysis for $C_{28}H_{28}N_6O_3$ | | |
|---|---|---|
| C (%) | H (%) | N (%) |
| Calcd: C, 67.73; | H, 5.68; | N, 16.92 |
| Found: C, 67.43; | H, 5.67; | N, 16.74 |

$^1$H-NMR (200 MHz, CDCl$_3$) δ: 0.92(3H, t), 1.33–1.52(2H, m), 1.69–1.85(2H, m), 2.75(2H, t), 3.99(2H, dd), 4.17(2H, dd), 5.36(2H, s), 7.13(4H, s), 7.29–7.41(2H, m), 7.48–7.61(4H, m), 8.02–8.06(1H, m)

WORKING EXAMPLE 56

2-Propyl-3-[[2'-(1H-tetrazol-5-yl)biphenyl-4-yl]methyl]-4(3H)-quinazolinone

A mixture of 2-propyl-3-[[2'-(N-trityltetrazol-5-yl)biphenyl-4-yl]methyl]-4(3H)-quinazoline (200 mg) in water (2 ml) and trifluoroacetic acid (6 ml) was stirred at room temperature for 1 hour and poured into water (20 ml). The precipitate was filtered off, washed with water, dried to give pale yellow powder, which was recrystallized from EtOAc-isopropyl ether to give colorless fine crystals (36 mg, 28%), mp 171°–172° C.

| Elemental Analysis for $C_{25}H_{22}N_6O$ | | |
|---|---|---|
| C (%) | H (%) | N (%) |
| Calcd: C, 71.07; | H, 5.25; | N, 19.89 |
| Found: C, 70.88; | H, 5.12; | N, 19.65 |

$^1$H-NMR (200 MHz, DMSO-d$_6$) δ: 0.91(3H, t), 1.72(2H, m), 2.71(2H, t), 5.39(2H, s), 7.07(2H, q), 7.13(2H, q), 7.15–7.35(1H, m), 7.50–7.75(5H, m), 7.84(1H, m), 8.16(1H, dd)

The following compounds were prepared according to the procedure for Working Example 56.

WORKING EXAMPLE 57

2-Methyl-3-[[2'-(1H-tetrazol-5-yl)biphenyl-4-yl]methyl]-4(3H)-quinazolinone mp 171°–172° C. (53% yield).

| Elemental Analysis for $C_{23}H_{18}N_6O \cdot 0.5H_2O$ | | |
|---|---|---|
| C (%) | H (%) | N (%) |
| Calcd: C, 68.47; | H, 4.75; | N, 20.83 |
| Found: C, 68.62; | H, 4.71; | N, 20.54 |

$^1$H-NMR (200 MHz, DMSO-d$_6$) δ: 2.49(3H, s), 5.38(2H, s), 7.07(2H, q), 7.15(2H, q), 7.45–7.75(6H, m), 7.83(1H, ddd), 8.16(1H, dd)

WORKING EXAMPLE 58

2-Ethyl-3-[[2'-(1H-tetrazol-5-yl)biphenyl-4-yl]methyl]-4(3H)-quinazolinone mp 225°–228° C. (23% yield).

| Elemental Analysis for $C_{24}H_{20}N_6O$ | | | | | |
|---|---|---|---|---|---|
| | C | (%) | H (%) | N | (%) |
| Calcd: | C, | 70.57; | H, 4.94; | N, | 20.57 |
| Found: | C, | 70.30; | H, 5.15; | N, | 20.45 |

$^1$H-NMR (200 MHz, DMSO-$d_6$) δ: 1.208(3H, t, J=7.4 Hz), 2.769(2H, q, J=7.4 Hz), 5.399(2H, s), 6.95–7.2(1H, m), 7.0675, 7.127(each 3H, AB type, J=8.6 Hz), 7.48–7.73(5H, m), 7.832(1H, dt, J=7.2 Hz, J'=1.2 Hz), 8.1705(1H, dd, J=8.0 Hz, J'=1.4 Hz)

WORKING EXAMPLE 59

2-Ethylthio-3-[[2'-(1H-tetrazol-5-yl)biphenyl-4-yl]methyl]-4(3H)-quinazolinone mp 196°–198° C. (23% yield).

| Elemental Analysis for $C_{24}H_{20}N_6OS$ | | | | | |
|---|---|---|---|---|---|
| | C | (%) | H (%) | N | (%) |
| Calcd: | C, | 66.07; | H, 4.62; | N, | 18.53 |
| Found: | C, | 65.78; | H, 4.65; | N, | 18.33 |

$^1$H-NMR (200 MHz, DMSO-$d_6$) δ: 1.34(3H, t), 3.25(2H, q), 5.32(2H, s), 7.06(2H, d), 7.20(2H, d), 7.40–7.75(6H, m), 7.82(1H, t), 8.122(1H, d).

WORKING EXAMPLE 60

2-Ethoxy-3-[[2'-(1H-tetrazol-5-yl)biphenyl-4-yl]methyl]-4(3H)-quinazolinone mp 210°–212° C.

| Elemental Analysis for $C_{24}H_{20}N_6OS$ | | | | | |
|---|---|---|---|---|---|
| | C | (%) | H (%) | N | (%) |
| Calcd: | C, | 67.91; | H, 4.75; | N, | 19.80 |
| Found: | C, | 68.17; | H, 4.55; | N, | 19.66 |

$^1$H-NMR (200 MHz, DMSO-$d_6$) δ: 1.31(3H, t), 4.47(2H, q), 5.19(2H, s), 7.05(2H, q), 7.21(2H, q), 7.30–7.65(6H, m), 7.74(1H, ddd), 8.08(1H, dd).

WORKING EXAMPLE 61

2-Butyl-5-methoxycarbonyl-3-[[2'-(1H-tetrazol-5-yl)biphenyl-4-yl]-methyl]-4(3H)-quinazolinone The title compound was prepared from the compound of Working Example 22b according to the procedure for Working Example 23.

mp 133°–143° C. (51% yield).

| Elemental Analysis for $C_{28}H_{26}N_6O_3 \cdot 0.3H_2O$ | | | | | |
|---|---|---|---|---|---|
| | C | (%) | H (%) | N | (%) |
| Calcd: | C, | 67.27; | H, 5.36; | N, | 16.81 |
| Found: | C, | 67.28; | H, 5.24; | N, | 16.63 |

$^1$H-NMR (CDCl$_3$) δ: 0.94(3H, t), 1.35–1.54(2H, m), 1.73–1.88(2H, m), 2.80(2H, t), 3.96(3H, s), 5.34(2H, s), 7.15(4H, s), 7.37–7.62(4H, m), 7.75–7.77(2H, m), 8.03–8.08(1H, m)

PHARMACEUTICAL EXAMPLES

The compounds (I) of the present invention are employed, for example, when used as agents for treating circulatory system diseases such as hypertension, heart diseases, strokes and the like, in the following formulations.

1. Capsule

| | |
|---|---|
| (1) 2-n-Butyl-6-(2-hydroxyethoxy)-3-[[2'-tetrazol-5-yl)-biphenyl-4-yl]methyl]-4(3H)-quinazolinone | 10 mg |
| (2) Lactose | 90 mg |
| (3) Microcrystalline cellulose | 70 mg |
| (4) Magnesium stearate | 10 mg |
| One capsule | 180 mg |

The ingredients (1), (2), and (3) and a half of the ingredient (4) were blended together and granulated. To this mixture was added the remaining half of the ingredient (4) and distributed into gelatin capsules.

2. Tablet

| | |
|---|---|
| (1) 2-n-Butyl-6-(2-hydroxyethoxy)-3-[[2'-tetrazol-5-yl)-biphenyl-4-yl]methyl]-4(3H)-quinazolinone | 10 mg |
| (2) Lactose | 35 mg |
| (3) Maize starch | 150 mg |
| (4) Microcrystalline cellulose | 30 mg |
| (5) Magnesium stearate | 5 mg |
| One tablet | 230 mg |

Each of the ingredients (1), (2), (3) and two-thirds (4) and a half of the ingredient (5) were blended together and granulated. To these granules were added the remaining ingredients (4) and (5) and then compressed to form tablets.

3. Injection

| | |
|---|---|
| (1) 2-n-Butyl-6-(2-hydroxyethoxy)-3-[[2'-tetrazol-5-yl)biphenyl-4-yl]methyl]-4(3H0-quinazolinone.sodium salt | 10 mg |
| (2) Inositol | 100 mg |
| (3) Benzyl alcohol | 20 mg |
| One ampule | 130 mg |

The ingredients (1), (2) and (3) were dissolved in distilled water for injection to a total volume of two ml and distributed into ampules. Total processes were carried out under sterile conditions.

EXPERIMENTAL EXAMPLE 1

Inhibition of binding of angiotensin-II to angiotensin receptor

Method

An experiment of inhibition on the binding of angiotensin-II (A-II) to A-II-receptor was conducted by modifying the method of Douglas et al. [Endocrinology, 102, 685–696 (1978)]. An A-II-receptor was prepared from the membrane fraction of bovine adrenal cortex.

The compound of the present invention ($10^{-9}$M to $3\times10^{-5}$M) and $^{125}$I-A-II (1.85 kBq/50 μl) were added to the receptor membrane fraction, and the mixture was incubated at room temperature for one hour. The receptor-bound and free $^{125}$I-A-II were separated through a filter (Whatman GF/B filter), and the radioactivity of $^{125}$I-A-II bound to the receptor was measured.

Results

The results relating to the compounds of the present invention are shown in Table 8.

EXPERIMENTAL EXAMPLE 2

Inhibitory Effect of the Compound of the Present Invention on Pressor Action of A-II

Method

Jcl: SD rats (9 week old, male) were used. On the day previous to the experiment, these animals were applied with cannulation into the femoral artery and vein under anesthesia with pentobarbital Na. The animals were fasted but allowed free access to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of A-II (100 ng/kg) as the control was measured. The drugs were orally administered, and then, at each point of the measurement, A-II was administered intravenously, and the pressor action was similarly measured. By comparing the pressor action before and after administration of the drug, the precent inhibition by the drug on A-II-induced pressor action was evaluated.

Results

The results relating to the compounds of the present invention are shown in Table 8.

TABLE 8

| Working Example | Radio Receptor Assay $10^{-7}$ (M) | (% Inhibition) $10^{-6}$ (M) | Pressor Response (30 mg/Kg, p.o.) |
|---|---|---|---|
| 1 | 24 | 67 | NT*a |
| 2 | 25 | 67 | NT |
| 3 | 28 | 71 | NT |
| 4 | 31 | 72 | NT |
| 8 | 29 | 73 | NT |
| 10 | 32 | 75 | NT |
| 11 | 29 | 70 | NT |
| 13 | 30 | 73 | NT |
| 16 | 31 | 68 | NT |
| 23 | 46 | 85 | +*b |
| 24 | 3 | 41 | NT |
| 25 | 18 | 58 | NT |
| 26 | 36 | 74 | + |
| 29 | 66 | 92 | + |
| 32 | 72 | 93 | + |
| 37 | 77 | 97 | + |
| 38 | 59 | 89 | + |
| 39 | 69 | 92 | + |
| 41 | 48 | 83 | + |
| 48 | 81 | 95 | NT |
| 49 | 63 | 88 | NT |
| 50 | 73 | 95 | NT |
| 53 | 76 | 92 | + |
| 54 | 74 | 88 | + |
| 55 | 75 | 94 | + |

*a NT, not tested.
*b (% Inhibition), + ≧70%.

What is claimed is:

1. A compound of the formula:

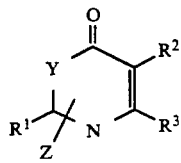

wherein Y is CH; $R^1$, optionally bound through a hetero atom, is (i) a hydrocarbon residue which may be substituted or (ii) a heteroaryl group; $R^2$ and $R^3$ which are the same or different, are each independently hydrogen, cyano, nitro, optionally substituted lower alkyl, or —COD wherein D is alkoxy, hydroxy, halogen, or optionally substituted amino; the dotted line is a chemical bond; Z is bound to a hetero nitrogen atom and is a group having the formula:

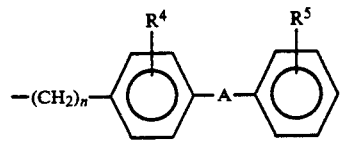

wherein $R^4$ is hydrogen, halogen or nitro, and $R^5$ is a residue capable of forming an anion or a residue convertible into an anion; A is a direct bond or a spacer having atomic length of two or less between the phenylene group and the phenyl group; and n is an integer of 1 or 2; or a pharmaceutically acceptable salt thereof.

2. A compound of claim 1 wherein $R^2$ is —COD wherein D is alkoxy, hydroxy, halogen or an optionally substituted amino; and $R^3$ is hydrogen or a pharmaceutically acceptable salt thereof.

3. A compound of claim 1 wherein $R^1$ is $C_{1-8}$ alkyl; $R^2$ is —COD wherein D is halogen, $C_{1-4}$ alkoxy, hydroxy or optionally substituted amino; and $R^3$ is hydrogen or a pharmaceutically acceptable salt thereof.

4. A pharmaceutical composition for antagonizing angiotensin II which comprises a therapeutically effective amount of a compound of claim 1 or a pharmaceutically acceptable salt thereof in admixture with a pharmaceutically acceptable carrier, excipient or diluent.

5. A compound according to claim 1, wherein $R^1$ is an acyclic or cyclic hydrocarbon residue which is optionally substituted with hydroxyl, lower ($C_{1-4}$) alkoxy, lower ($C_{1-4}$) alkyl, halogen, nitro, optionally substituted amino, acyloxy, or aryl which may be optionally substituted with halogen, nitro, lower ($C_{1-4}$) alkoxy, or lower ($C_{1-4}$) alkyl on the benzene ring.

6. A compound according to claim 5, wherein the acyclic hydrocarbon residue is a lower alkyl of 1 to 8 carbon atoms, lower alkenyl of 2 to 8 carbon atoms, or lower alkynyl of 2 to 8 carbon atoms.

7. A compound according to claim 5, wherein the cyclic hydrocarbon residue is an alicyclic hydrocarbon residue of 3 to 8 carbon atoms or an aromatic hydrocarbon residue of 6 to 12 carbon atoms.

8. A compound according to claim 5, wherein the optionally substituted amino group is amino, N-lower ($C_{1-4}$) alkyl amino, N,N-dilower ($C_{1-4}$) alkyl amino, N-arylamino, N-aralkylamino, or alicyclic amino.

9. A compound according to claim 5, wherein the acyloxy group is lower ($C_{1-4}$) alkanoyloxy, or aroyloxy.

10. A compound according to claim 1, wherein $R^2$ is lower ($C_{1-4}$) alkoxycarbonyl, carbamoyl, N-lower ($C_{1-4}$) alkylcarbamoyl, N,N-dilower ($C_{1-4}$) alkylcarbamoyl, N-arylcarbamoyl, N-aralkylcarbamoyl, N-heteroarylcarbamoyl, N-heteroaralkylcarbamoyl, or alicyclic carbamoyl, wherein said alkyl, aryl and heteroaryl groups are optionally substituted with alkyl, hydroxyl, optionally substituted amino, halogen, nitro, or lower ($C_{1-4}$) alkoxy.

11. A compound according to claim 1, wherein $R^2$ is straight or branched lower alkyl of 1 to about 8 carbon atoms optionally substituted with hydroxyl, lower ($C_{1-4}$) alkoxy, optionally esterified carboxyl, lower ($C_{1-4}$) alkyl, halogen, nitro, optionally substituted amino, acyloxy or aryl optionally substituted with halogen, nitro, lower ($C_{1-4}$) alkoxy, or lower ($C_{1-4}$) alkyl on the benzene ring.

12. A compound according to claim 1, wherein $R^2$ is straight or branched lower alkyl of 1 to 8 carbon atoms optionally substituted with hydroxyl, lower ($C_{1-4}$) alkoxy, lower ($C_{1-4}$) alkoxycarbonyl, lower ($C_{1-4}$) alkyl, halogen, nitro, amino, N-lower ($C_{1-4}$) alkyl amino, N,N-dilower ($C_{1-4}$) alkyl amino, N-arylamino, N-aralkylamino, alicyclic amino, lower ($C_{1-4}$) alkanoyloxy, aroyloxy or aryl optionally substituted with halogen, nitro, lower ($C_{1-4}$) alkoxy, or lower ($C_{1-4}$) alkyl on the benzene ring.

13. A method for antagonizing angiotensin II in a mammal which comprises administering to said mammal a therapeutically effective amount of a compound of claim 1 or a pharmaceutically acceptable salt thereof.

14. A compound of claim 2 which is ethyl 6-n-butyl-1-[[2'-(1H-tetrazol-5-yl)biphenyl-4-yl]-methyl]-4-oxo-1,4-dihydronicotinate.

15. A compound according to claim 1, wherein $R^4$ is hydrogen.

16. A compound according to claim 1, wherein $R^5$ is carboxyl, lower ($C_{1-4}$) alkoxycarbonyl, cyano, tetrazolyl, trifluoromethanesulfonic amide, phosphoric acid, or sulfonic acid.

17. A compound according to claim 1, wherein $R^5$ is carboxyl or tetrazolyl.

18. A compound according to claim 1, wherein $R^5$ is tetrazolyl.

19. A compound according to claim 1, wherein $R^5$ is in the ortho position.

20. A compound according to claim 1, wherein A is a direct bond, lower ($C_{1-4}$) alkylene,

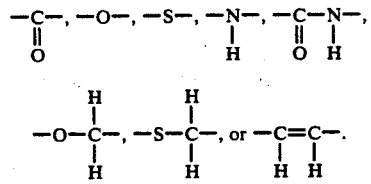

21. A compound of claim 1 wherein $R^1$ is optionally bound through a hetero atom which is nitrogen, oxygen or sulfur.

22. A compound of claim 1 wherein $R^1$ is optionally bound through a hetero atom which is nitrogen, oxygen or sulfur and said spacer is a divalent chain in which the number of atoms between the phenylene groups is up to 2.

23. A compound of claim 1 wherein $R^1$ is optionally bound through a hetero atom which is nitrogen, oxygen or sulfur and said spacer is a member selected from the group consisting of $C_{1-4}$ alkylene, —C(=O)—, —O—, —S—, —N(H)—, —C(=O)N(H)—, —OC($H^2$)—, —OS($H^2$)— and —C(H)=C(H)—.

* * * * *